United States Patent
Zamecnik et al.

(10) Patent No.: US 11,278,626 B2
(45) Date of Patent: Mar. 22, 2022

(54) COMPOSITIONS OF POLYMERIC NANOWIRES AND METHODS OF MAKING AND USING THEREOF

(71) Applicant: The Regents of the University of California, Oakland, CA (US)

(72) Inventors: Colin R. Zamecnik, Oakland, CA (US); Tejal A. Desai, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 130 days.

(21) Appl. No.: 16/338,103

(22) PCT Filed: Oct. 4, 2017

(86) PCT No.: PCT/US2017/055157
§ 371 (c)(1),
(2) Date: Mar. 29, 2019

(87) PCT Pub. No.: WO2018/067711
PCT Pub. Date: Apr. 12, 2018

(65) Prior Publication Data
US 2020/0023068 A1 Jan. 23, 2020

Related U.S. Application Data

(60) Provisional application No. 62/482,055, filed on Apr. 5, 2017, provisional application No. 62/404,691, filed on Oct. 5, 2016.

(51) Int. Cl.
| | | |
|---|---|---|
| *A61K 47/59* | (2017.01) | |
| *A61K 9/00* | (2006.01) | |
| *B82Y 5/00* | (2011.01) | |
| *B82Y 40/00* | (2011.01) | |
| *C07K 16/24* | (2006.01) | |

(52) U.S. Cl.
CPC .......... *A61K 47/593* (2017.08); *A61K 9/0019* (2013.01); *B82Y 5/00* (2013.01); *B82Y 40/00* (2013.01); *C07K 16/246* (2013.01)

(58) Field of Classification Search
CPC .... A61K 47/593; A61K 9/0019; B82Y 40/00; B82Y 15/00; B82Y 5/00
See application file for complete search history.

(56) References Cited

U.S. PATENT DOCUMENTS

| | | |
|---|---|---|
| 2011/0177154 A1 | 7/2011 | Bangera et al. |
| 2015/0238476 A1* | 8/2015 | Bosnyak .............. A61K 31/455 424/400 |

FOREIGN PATENT DOCUMENTS

WO 2016/100136 6/2016

OTHER PUBLICATIONS

Fox et al. (Nano. Lett., Mar. 11, 2015;15(3) 1540-1546 (IDS)) (Year: 2015).*
Du et al. (ACS Applied Materials & Interfaces; 2012, 4, 4643-4650) (Year: 2012).*
Jiang et al. (Handbook of Biopolymers ad Biodegradable plastics, 2013 Chapter 6 Biodegradable Polymers and Polymer Blends p. 120 section 6.4.1) (Year: 2013).*
Bechara et al. (Biomaterials 31 (2010) 3492-3501) (Year: 2010).*
Fox, et al. (2015) "Fabrication of Micro Patterned Polymeric Nanowire Arrays for High-Resolution Reagent Localization and Topographical Cellular Control", Nano Letters. vol. 15, No. 3. pp. 1540-1546.
Bechara, et al. (2010) "Template synthesized poly (@?-caprolactone) nanowire surfaces for neural tissue engineering", Biomaterials, Elsevier, Amsterdam, NL, vol. 31, No. 13, pp. 3492-3501.
Du, et al. (2012) "Cellular Interactions on Hierarchical Poly ([epsilon] -caprolactone), Nanowire Micropatterns", ACS Applied Materials & Interfaces, vol. 4, No. 9, pp. 4643-4650.
Porter, et al. (2009) "Biodegradable poly (@?-caprolactone) nanowires for bone tissue engineering applications", Biomaterials, Elsevier, Amsterdam, NL, vol. 30, No. 5, pp. 780-788.
Tao, et al. (2007) "Aligned Arrays of Biodegradable Poly ([epsilon] -caprolactone) Nanowires and Nanofibers by Template Synthesis", vol. 7, No. 6, pp. 1463-1468.

* cited by examiner

*Primary Examiner* — Anna R Falkowitz
(74) *Attorney, Agent, or Firm* — Edward J. Baba; Shweta Chandra; Bozicevic, Field & Francis LLP

(57) ABSTRACT

Aspects of the present disclosure include compositions having a plurality of individual polymeric nanowires. Individual polymeric nanowires according to embodiments include a bioactive compound. Methods for preparing and methods for administering the subject compositions of individual polymeric nanowires to a subject are also described. Kits having one or more components for practicing the subject methods are also provided.

29 Claims, 12 Drawing Sheets

COMPOSITIONS OF POLYMERIC NANOWIRES AND METHODS OF MAKING AND USING THEREOF

CROSS-REFERENCE TO RELATED APPLICATIONS

This application claims priority to U.S. Provisional Application No. 62/404,691, filed Oct. 5, 2016, and to U.S. Provisional Application No. 62/482,055, filed Apr. 5, 2017, each of which is incorporated herein by reference in its entirety.

INTRODUCTION

Nanowires and nanotubes are slender structures of metals, semiconductors, insulators and organic compounds and have been studied for use in electronics, energy conversion, optics and chemical sensing, among other fields. The interface between nanosystems and biosystems is a dynamic area of study where biology, chemistry, physics and many areas of engineering are—applied to biotechnology and medicine. Nanowires and nanotubes have been used as quasi-one dimensional probes that penentrate the plasma membrane of cells for use in high resolution and high throughput gene discovery, biosensing and single cell electrophysiology.

Discrete, free floating asymmetric nanostructures have distinct advantages over their spherical counterparts, such as higher surface area and greater residence time in vivo. Nanostructures having high aspect ratio find use as antifibrotics, where these topographical cues have been shown to decrease collagen secretion and other pro-fibrotic responses in both in vivo and in vitro models. Widespread use of assymetic nanostructures in bioengineering applications is however, limited.

SUMMARY

Aspects of the present disclosure include a composition having a plurality of individual polymeric nanowires in an aqueous solution. Individual polymeric nanowires according to embodiments include a bioactive compound. In some embodiments, the bioactive compound is contained within the pores of the polymeric nanowire. In other embodiments, the bioactive compound is bonded to an outer surface of each individual polymeric nanowire. In certain instances, the bioactive compound is covalently bonded to the outer surface of the polymeric nanowire through a linker, such as an enzymatically cleavable linker, a hydrolysable linker or other type of linker. Linkers of interest may be chemically substituted, such as with an aryl group. In certain embodiments, the linkers include a maleimidophenyl group. Individual polymeric nanowires in the subject compositions may have a diameter that ranges from 10 nm to 500 nm, such as about 200 nm. The length of the polymeric nanowires may be from 1 μm to 50 μm, such as from 10 μm to 20 μm. In embodiments, compositions of interest include a plurality of individual polymeric nanowires having an aspect ratio of 2 or higher, such as 5 or higher. Individual polymeric nanowires, according to certain embodiments, are configured to release bioactive compound at a substantially zero-order release rate. In other embodiments, individual polymeric nanowires are configured to release bioactive compound at a substantially first-order release rate.

Aspects of the present disclosure also include methods for administering the subject compositions to a subject. In practicing the subject methods according to certain embodiments, a composition of a plurality of individual polymeric nanowires having a bioactive compound is administered to a subject. In certain embodiments, the composition is formulated for injection into the subject and methods include injecting the composition of individual polymeric nanowires into the subject. In some instances, the plurality of individual polymeric nanowires localize in a target tissue a predetermined period of time after administration to the subject (e.g., after injection or intravenous infusion) In certain instances, 50% or more of the plurality of individual nanowires in the composition localizes in the target tissue. In other instances, 75% or more of the plurality of individual nanowires in the composition localizes in the target tissue.

The present disclosure also includes methods for preparing a composition having individual polymeric nanowires. In practicing methods according to certain embodiments, a polymer composition is applied to a surface of a substrate to produce a polymer-coated substrate, a template structure is positioned onto the polymer-coated substrate in a manner sufficient to draw an amount of polymer into the pores of the template structure and individual nanowires are removed from the template structure.

In embodiments, methods include coating a polymer composition having a polymer to the surface of a substrate. The polymer may have a molecular weight which varies, such as from 5 kDa to 250 kDa including from 40 kDa to 80 kDa. In some embodiments, the polymer is a polyester, such as polycaprolactone. In preparing the subject nanowires, the polymer-coated substrate may be further flattened, such as by removing solvent from the applied polymer composition or by heating the polymer-coated substrate.

In certain embodiments, the polymer-coated substrated is heated to draw the polymer into the pores of the template structure, forming each nanowire. The polymer-coated substrate may be heated to a temperature above the melting temperature of the polymer, such as a temperature that is from 5° C. to 100° C. above the melting temperature of the polymer. For example, where the polymer is polycaprolactone, the polycaprolactone-coated substrate may be heated to about 100° C. and the template structure is applied to the heated polycaprolactone-coated substrate to draw the polycaprolactone into the pores of the template structure. The nanowires are formed by maintaining the template structure on the polymer-coated substrate for a predetermined period of time. In certain embodiments, methods include maintaining the template structure on the polymer-coated substrate until the template structure comes into direct contact with the substrate. In these embodiments, substantially all of the polymer is drawn from the surface of the substrate and into the pores of the template.

The template structure may be a porous membrane, such as a porous metal or porous metal oxide membrane. In certain instances, the template structure is a porous aluminum oxide membrane. Depending on the desired length of the nanowires, the thickness of the template structure may vary, ranging from 1 μm to 50 μm, such as from 10 μm to 20 μm. The pores of the template structure may also vary, ranging from 10 nm to 500 nm, such as from 20 nm to 200 nm. In certain embodiments, the template structure has 200 nm pores.

To remove the nanowires from the template structure, methods may include etching the template structure. In some instances, the polymeric nanowires are removed from the template structure by contacting the template structure containing the nanowires with a base, such as sodium hydroxide. In certain embodiments, the nanowires are removed by dissolving the template structure in the base. The subject nanowires removed from the template may have diameters of from 10 nm to 500 nm, such as from 20 nm to 200 nm, including 200 nm. The length of the nanowires may range from 1 µm to 50 µm, such as from 10 µm to 25 µm, such as 20 µm. Nanowires of interest may have aspect ratios of 2 or greater, such as 5 or greater. In certain embodiments, the subject individual polymeric nanowires do not have a lumen. The composition of individual polymeric nanowires removed from the template structure may be further purified, such as by filtering the composition with deionized water or a buffer solution.

In some embodiments, methods further include contacting the composition of individual polymeric nanowires with one or more bioactive compounds. In certain instances, contacting the composition of individual polymeric nanowires with one or more bioactive compounds includes mixing the individual polymeric nanowires with one or more bioactive compounds in a manner sufficient to fill one or more pores in each individual polymeric nanowire with bioactive compound. In other instances, contacting the composition of individual polymeric nanowires with one or more bioactive compounds include covalently bonding bioactive compound to an outer surface of the each individual polymeric nanowire. The bioactive compound may be directly bonded to the outer surface of the polymeric nanowire or may be coupled through a linker, such as an enzymatically cleavable linker or a hydrolysable linker. Covalently bonding the bioactive compound to each individual polymeric nanowire, in certain embodiments, includes contacting the composition of individual polymeric nanowires with a composition having an aryl isocyanate (e.g., maleimidophenyl isocyanate) to produce an activated individual polymeric nanowire precursor composition and contacting the activated individual polymeric nanowire precursor composition with the bioactive compound to produce a composition having individual polymeric nanowires covalently bonded to the bioactive compound.

DETAILED DESCRIPTION

Figure 1:
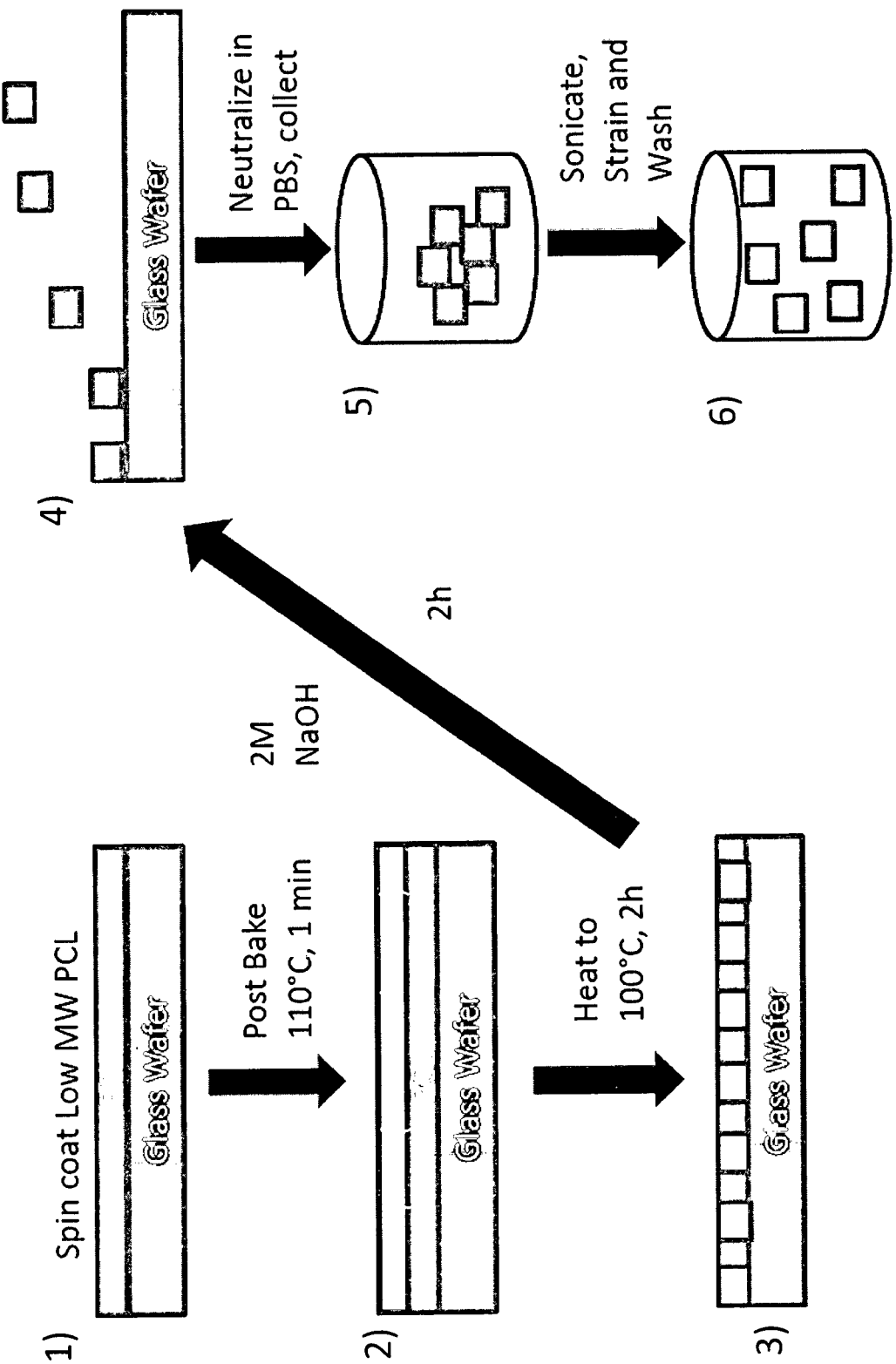
FIG. 1 depicts preparing a composition having individual, free-floating polymeric nanowires according to certain embodiments of the present disclosure.

Aspects of the present disclosure include compositions having a plurality of individual polymeric nanowires. Individual polymeric nanowires according to embodiments include a bioactive compound. Methods for preparing and methods for administering the subject compositions of individual polymeric nanowires to a subject are also described. Kits having one or more components for practicing the subject methods are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing embodiments of the invention, compositions of individual polymeric nanowires having a bioactive compound are first reviewed in greater detail. Next, methods for using the polymeric nanowire compositions are provided. Methods for preparing a composition having individual polymeric nanowires and kits having one or more components from practicing the subject methods are also described.

Compositions of Individual Polymeric Nanowires

As summarized above, aspects of the present disclosure compositions of individual polymeric nanowires. In embodiments, individual polymeric nanowires include one or more bioactive compounds. The term "individual polymeric nanowires" as used herein refers to a composition that includes discrete, free-floating polymeric nanowires in a fluidic solution where each individual nanowire is not joined to any other nanowire in the solution. In particular, individual polymeric nanowires of the subject compositions are not connected together to each other (e.g., covalently bonded) or affixed to a common substrate. As described in greater detail below, the individual polymeric nanowires are formed in a vertical array of parallel pores of a template structure and are removed so that there is no permanent connection between each polymeric nanowire or a bond between the polymeric nanowires and a substrate.

In embodiments, polymeric nanowires include one or more bioactive compounds. The bioactive compounds may be absorbed into pores of the polymeric nanowires or may be affixed to a surface of the polymeric nanowire, such as by non-covalent interactions (e.g., ionic forces, dipole-dipole interactions, hydrogen bonding) or by one or more covalent bonds. As described in greater detail below, the subject polymeric nanowires are configured to deliver the one or more bioactive compounds to a target site, such as by injecting the composition into a target site, localization of the polymeric nanowires after ingesting, nasal inhalation or intravenous delivery or through release of the polymeric nanowires from an implanted device at the target site.

Suitable bioactive compounds may include but are not limited to interferon, interleukin, erythropoietin, granulocyte-colony stimulating factor (GCSF), stem cell factor (SCI:), leptin (OB protein), interferon (alpha, beta, gamma), antibiotics such as vancomycin, gentamicin ciprofloxacin, amoxycillin, lactobacillus, cefotaxime, levofloxacin, cefipime, mebendazole, ampicillin, lactobacillus, cloxacillin, norfloxacin, tinidazole, cefpodoxime, proxctil, azithromycin, gatifloxacin, roxithromycin, cephalosporin, anti-thrombogenics, aspirin, ticlopidine, sulfinpyrazone, heparin, warfarin, growth factors, differentiation factors, hepatocyte stimulating factor, plasmacytoma growth factor, glial derived neurotrophic factor (GDNF), neurotrophic factor 3 (NT3), fibroblast growth factor (FGF), transforming growth factor (TGF), platelet transforming growth factor, milk growth factor, endothelial growth factors, endothelial cell-derived growth factors (ECDGF), alpha-endothelial growth factors, beta-endothelial growth factor, neurotrophic growth factor, nerve growth factor (NGF), vascular endothelial growth factor (VEGF), 4-1 BB receptor (4-IBBR), TRAIL (TNF-related apoptosis inducing ligand), artemin (GFRalpha3-RET ligand), BCA-I (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, thrombopoietin, megakaryocyte derived growth factor (MDGF), keratinocyte growth factor (KGF), platelet-derived growth factor (PDGF), ciliary neurotrophic factor (CNTF), neurotrophin 4 (NT4), granulocyte colony-stimulating factor (GCSF), macrophage colony-stimulating factor (mCSF), bone morphogenetic protein 2 (BMP2), BRAK, C-IO, Cardiotrophin 1 (CT1), CCR8, anti-inflammatory: paracetamol, salsalate, diflunisal, mefenamic acid, diclofenac, piroxicam, ketoprofen, dipyrone, acetylsalicylic acid, anti-cancer drugs such as aliteretinoin, altertamine, anastrozole, azathioprine, bicalutarnide, busulfan, capecitabine, carboplatin, cisplatin, cyclophosphamide, cytarabine, doxorubicin, epirubicin, etoposide, exemestane, vincristine, vinorelbine, hormones, thyroid stimulating hormone (TSH), sex hormone binding globulin (SHBG), prolactin, luteotropic hormone (LTH), lactogenic hormone, parathyroid hormone (PTH), melanin concentrating hormone (MCH), luteinizing hormone (LHb), growth hormone (HGH), follicle stimulating hormone (FSHb), haloperidol, indomethacin, doxorubicin, epirubicin, amphotericin B, Taxol, cyclophosphamide, cisplatin, methotrexate, pyrene, amphotericin B, anti-dyskinesia agents, Alzheimer vaccine, antiparkinson agents, ions, edetic acid, nutrients, glucocorticoids, heparin, anticoagulation agents, antivirus agents, anti-HIV agents, polyamine, histamine and derivatives thereof, cystineamine and derivatives thereof, diphenhydramine and derivatives, orphenadrine and derivatives, muscarinic antagonist, phenoxybenzamine and derivatives thereof, protein A, streptavidin, amino acid, beta-galactosidase, methylene blue, protein kinases, beta-amyloid, lipopolysaccharides, eukaryotic initiation factor-4G, tumor necrosis factor (TNF), tumor necrosis factor-binding protein (TNF-bp), interleukin-1 (to 18) receptor antagonist (IL-Ira), granulocyte macrophage colony stimulating factor (GM-CSF), novel erythropoiesis stimulating protein (NESP), thrombopoietin, tissue plasminogen activator (TPA), urokinase, streptokinase, kallikrein, insulin, steroid, acetaminophen, analgesics, antitumor preparations, anti-cancer preparations, anti-proliferative preparations or pro-apoptotic preparations, among other types of bioactive agents.

The amount of bioactive compound will depend on the site of application, the condition being treated and the type of bioactivity desired. In some embodiments, individual polymeric nanowires may include 0.001 ng or greater of the bioactive agent, such as 0.01 ng or greater, 0.0001 µg or greater of the bioactive compound, such as 0.001 µg or greater, such as 0.01 µg or greater, such as 0.1 µg or greater, such as 1 µg or greater, such as 10 µg or greater, such as 25 µg or greater, such as 50 µg or greater, such as 100 µg or greater such as 500 µg or greater, such as 1000 µg or greater such as 5000 µg or greater and including 10,000 µg or greater. Where the bioactive compound is incorporated into the polymeric nanowires as a liquid, the concentration of bioactive compound may be 0.0001 ng/mL or greater, such as 0.001 ng/mL or greater, such as 0.01 ng/mL or greater, such as 0.1 ng/mL or greater, such as 0.5 ng/mL or greater, such as 1 ng/mL or greater, such as 2 ng/mL or greater, such as 5 ng/mL or greater, such as 10 ng/mL or greater, such as 25 ng/mL or greater, such as 50 ng/mL or greater, such as 100 ng/mL or greater such as 500 ng/mL or greater, such as 1000 ng/mL or greater such as 5000 ng/mL or greater and including 10,000 ng/mL or greater.

Depending on the amount of bioactive compound associated with the individual polymeric nanowires, compositions of individual polymeric nanowires have a concentration of bioactive compound that is 0.001 nM or greater, such as 0.005 nM or greater, such as 0.01 nM or greater, such as 0.05 nM or greater, such as 0.1 nM or greater, such as 0.5 nM or greater, such as 1 nM or greater, such as 5 nM or greater, such as 10 nM or greater, such as 50 nM of greater, such as 100 nM or greater, such as 250 nM or greater and including 500 nM or greater.

Where the bioactive compound is incorporated into the pores of the polymer nanowires, the bioactive compound may be introduced into the pores of the polymeric nanowires by any convenient protocol. In certain embodiments, as described in greater detail below, the one or more bioactive compounds are incorporated into the polymeric nanowires by incubating the individual polymeric nanowires in the presence of the one or more bioactive compounds with or without a solvent for a predetermined amount of time, such as for 1 hour or more, 5 hours or more, 10 hours or more, 12 hours or more, 24 hours or more, 3 days or more and including 1 week or more, to allow the polymeric nanowires to incorporate one of more bioactive compounds into the pores of the polymeric nanowire. Still further, the one or more bioactive compounds may be added directly to the basic component mixture of the polymeric nanowires such that during fabrication, the one or more bioactive compounds may be incorporated into the final individual polymeric nanowires.

Where the individual polymeric nanowires incorporate bioactive compound into pores, the cross-sectional shape and size of each pore may vary. In embodiments, the cross-sectional shape of pores incorporating bioactive compound into the polymeric nanowires may be a circle, a semi-circle, oval, moon-shaped, crescent shaped, polygonal or other shape or a combination thereof. In some embodiments the cross-sectional shape of pores incorporating bioactive compound into the polymeric nanowires is a circle. In other embodiments, the cross-sectional shape of pores incorporating bioactive compound into the polymeric nanowires is polygonal, e.g., square, rectangle, pentagon, hexagon, octagon or some other polygon. In still other embodiments, the cross-sectional shape of pores incorporating bioactive compound into the polymeric nanowires is oval. The diameter of the pores may be is 0.001 µm or more, such as 0.005 µm or more, such as 0.01 µm or more, such as 0.05 µm or more, such as 0.1 µm or more, such as 0.2 µm or more, such as 0.3 µm or more, such as 0.5 µm or more, such as 1.0 µm or more, such as 1.5 µm or more, such as 2.0 µm or more, such as 2.5 µm or more, such as 3.0 µm or more, such as 5.0 µm or more, such as 10 µm or more, such as 15 µm or more, such as 20 µm or more and including 25 µm or more. In certain embodiments, pores incorporating bioactive compound into the have a diameter ranging from 0.01 µm to 0.5 µm. The depth of the pores may also vary, ranging from 0.0001 µm to 0.01 µm, such as from 0.0005 µm to 0.005 µm and including from 0.001 µm to 0.005 µm.

As described in greater detail below, the bioactive compound may be covalently bonded to the polymeric nanowires, such as to the surface of each individual polymeric nanowire. In some embodiments, the bioactive compound is directly bonded to the polymeric nanowires. In other embodiments the bioactive compound is bonded to the polymeric nanowires through a linker. Any number of bioactive compounds may be bonded to each individual polymeric nanowire (e.g., on the outer surface), such as one bioactive compound or more, such as 2 bioactive compound or more, such as 3 bioactive compound or more, such as 5 bioactive compounds or more, such as 10 bioactive compounds or more, such as 15 bioactive compounds or more and including 25 bioactive compounds or more bonded to each individual polymeric nanowire. Each individual polymeric nanowire may have more than one type of bioactive compound covalently bonded, such as 2 different types of bioactive compounds or more, such as 3 different types of bioactive compounds or more, such as 5 different types of bioactive compounds or more, such as 10 different types of bioactive compounds or more, such as 15 different types of bioactive compounds and including 25 different types of bioactive compounds or more.

The bioactive compound may be covalently bonded to the polymer nanowire by any convenient protocol, including but not limited to addition reactions, elimination reactions, substitution reactions, pericyclic reactions, photochemical reactions, redox reactions, radical reactions, reactions through a carbene intermediate, metathesis reaction, among other types of bond-forming reactions. For example, the polymeric nanowire may be covalently bonded to the bioactive compound through a Michael addition reaction, including thiol alkene and thiol alkyne, biotin avidin interactions, formation of amide bonds via EDC NHS, thiol exchange reactions, tetrazine ligation, azide mediated linkages, cyclooctyne and other strained cycloaddition reactions In some embodiments, the bioactive compound is covalently bonded to the polymeric nanowire through reactive linking chemistry such as where reactive linker pairs include, but is not limited to: maleimide/thiol; maleimide/alcohol; thiol/thiol; pyridyldithiol/thiol; succinimidyl iodoacetate/thiol; N-succinimidylester (NHS ester), sulfodichlorophenol ester (SDP ester), or pentafluorophenyl-ester (PFP ester)/amine; bissuccinimidylester/amine; imidoesters/amines; hydrazine or amine/aldehyde, dialdehyde or benzaldehyde; isocyanate/hydroxyl or amine; carbohydrate-periodate/hydrazine or amine; diazirine/aryl azide chemistry; pyridyldithiol/aryl azide chemistry; alkyne/azide; carboxycarbodiimide/amine; amine/Sulfo-SMCC (Sulfosuccinimidyl 4-[N-maleimidomethyl]cyclohexane-1-carboxylateythiol and amine/BMPH (N-[β-Maleimidopropionic acid] hydrazide.TFA)/thiol; azide/triarylphosphine; nitrone/cyclooctyne; azide/tetrazine and formylbenzamide/hydrazino-nicotinamide. In certain embodiments, linkers of interest include an aryl linker, such as a p-maleimido aryl linker. For example, each individual polymeric nanowire may be covalently bonded to the bioactive compound with a maleimide-thiol reaction, such as through a p-maleimidophenyl linker. In certain embodiments, the bioactive compound is covalently bonded to the polymeric nanowire through a biological macromolecule linker, such as a polysaccharide linker, a peptide linker, an amino acid linker, a nucleic acid linker, a polynucleotide linker.

In certain embodiments, the polymeric nanowires are formulated to release the one or more bioactive compounds at a target site. In one example, the one or more bioactive compounds are released from the within the pores of each individual polymeric nanowire in the subject compositions. In another example, the one or more bioactive compounds are released by cleavage of a linker between the polymeric nanowire and the bioactive compound. For example, the linker may be enzymatically cleaved or cleaved by hydrolysis. Where the linker is enzymatically cleaved, linkers of interest may include enzymatically cleavable moiety, such as moieties cleavable by digestive enzymes including, but not limited to proteolytic enzymes, lipolytic enzymes, amylolytic enzymes and nucleolytic enzymes, ptyalin, amylase, betaine, bromelain, pepsin, gastric amylase, gelatinase, rennin, gastic lipase, pancreatic lipase, phospholipase, trypsin, steapsin, chymotrypsin, collagenase, hyaluroidase, carboxypeptidase, pancreatic amylase, elastases, nucleases, DNase I, sucrase, maltase, lactase, isomaltase, matrix metalloproteinases, among other digestive enzymes.

Release of the bioactive compound by the polymeric nanowires may be a sustained release or pulsatile release. By "sustained release" is meant that the bioactive compound is associated with the polymeric nanowires to provide for constant and continuous delivery of one or more bioactive compounds over the entire time the polymeric nanowires are maintained in contact with the site of administration, such as over the course of 1 minute or longer, such as 5 minutes or longer, such as 10 minutes or longer, such as 15 minutes or longer, such as 30 minutes or longer, such as 45 minutes or longer, such as 1 hour or longer, such as 6 hours or longer, such as 12 hours or longer, such as 1 day or longer, such as 2 days or longer, such as 5 days or longer, such as 10 days or longer, such as 15 days or longer, such as 30 days or longer and including 100 days or longer. For example, the bioactive compound may be associated with the polymeric nanowires to provide for constant and continuous delivery over that ranges, such as from 1 day to 30 days, such as from 2 days to 28 days, such as from 3 days to 21 days, such as from 4 days to 14 days and including from 5 days to 10 days.

In other instances, the individual polymeric nanowires are configured to provide a pulsatile release of the one or more bioactive compound. By "pulsatile release" is meant that the polymeric nanowires release the one or more bioactive compounds into the site of administration incrementally (e.g., at discrete times), such as every 1 minute, such as every 5 minutes, such as every 10 minutes, such as every 15 minutes, such as every 30 minutes, such as every 45 minutes, 1 hour, such as every 2 hours, such as every 5 hours, such as every 12 hours, such as every 24 hours, such as every 36 hours, such as every 48 hours, such as every 72 hours, such as every 96 hours, such as every 120 hours, such as every 144 hours and including every 168 hours or some other increment.

In other instances, the subject polymeric nanowires are degradable over time and deliver the one or more bioactive compounds after a certain amount of the polymeric nanowire has degraded. For example, an amount of the one or more bioactive compounds may be delivered after every 10% of the polymeric nanowire has degraded, such as after every 15% of the polymeric nanowire has degraded, such as after every 20% of the polymeric nanowire has degraded, such as after every 25% of the polymeric nanowire has degraded, such as after every 30% of the polymeric nanowire has degraded and including after after every 33% of the polymeric nanowire has degraded at the site of administration.

In yet other instances, individual polymeric nanowires of the present disclosure release a large amount of the one or more bioactive compounds immediately upon administration at the target site, such as for example 50% or more, such as 60% or more, such as 70% or more and including 90% or more of the one or more bioactive compounds are released immediately upon administration. In yet other instances, the individual polymeric nanowires release the one or more bioactive compounds at a predetermined rate, such as at a substantially zero-order release rate, such as at a substantially first-order release rate or at a substantially second-order release rate.

In certain embodiments, the individual polymeric nanowires of the present disclosure provide for a release profile of the bioactive compound, where the release profile includes:

a first period where the bioactive compound is released from the polymeric nanowire at a first predetermined rate; and a second period where the bioactive compound is released from the polymeric nanowire at a second predetermined rate.

For example, in these embodiments, the first period may be a duration ranging from 0.1 hours to 72 hours from the administration time of the subject compositions, such as from 0.2 hours to 65 hours, such as from 0.5 hours to 60 hours, such as from 1 hour to 50 hours, such as from 2 hours to 48 hours, such as from 3 hours to 36 hours, such as from 4 hours to 30 hours and including from 5 hours to 24 hours from the time of administration. The second period may be a duration ranging from 0.5 hours to 336 hours from the administration time of the composition, such as from 1 hour to 312 hours, such as from 2 hours to 288 hours, such as from 3 hours to 264 hours, such as from 4 hours to 240 hours, such as from 5 hours to 216 hours and including from 6 hours to 192 hours from the time of administration.

The release rate of the bioactive compound during each respective period during the release profile may vary depending on how the polymeric nanowires are structured as well has the type of association between the polymeric nanowires and the bioactive compound (e.g., filled within the pores of the polymeric nanowires, covalently bonded). In some embodiments, the first predetermined rate may be a substantially zero-order release rate. In other embodiments the first predetermined rate may be a substantially first-order release rate. In yet other embodiments the first predetermined rate may be a second-order release rate. Similarly, the second predetermined rate may be a substantially zero-order release rate, a substantially first-order release rate or a substantially second-order release rate.

In certain embodiments, the release profile includes a first period having a substantially first order release rate followed by a second period having a substantially zero order release rate. In other embodiments, the release profile includes a first period having a substantially second order release rate followed by a second period having a substantially first order release rate. In yet other embodiments, the release profile includes a first period having a substantially second order release rate followed by a second period having a substantially zero order release rate.

In these embodiments, the amount of the bioactive compound released during each respective period may vary. In some instances, the individual polymeric nanowires release between 10% and 75% of the total amount of bioactive compound during the first period, such as between 15% and 70% of the total amount of bioactive compound, such as between 20% and 60% of the total amount of bioactive compound, such as between 25% and 50% of the total amount of bioactive compound and including between 30% and 35% of the total bioactive compound during the first period. In these instances, the individual polymeric nanowires release between 10% and 75% of the total amount of bioactive compound during the second period, such as between 15% and 70% of the total amount of bioactive compound, such as between 20% and 60% of the total amount of bioactive compound, such as between 25% and 50% of the total amount of bioactive compound and including between 30% and 35% of the total bioactive compound during the second period.

Where more than one bioactive compound is delivered, the amount (i.e., mass) of each of bioactive compound in the subject compositions may vary, ranging from 0.001 mg to 1000 mg, such as 0.01 mg to 500 mg, such as 0.1 mg to 250 mg, such as 0.5 mg to 100 mg, such as 1 mg to 50 mg, including 1 mg to 10 mg. As such, in compositions of the present disclosure, the mass ratio of the first bioactive compound to other (i.e., second or more) bioactive compound may vary, and in some instances may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the first bioactive compound to other (i.e., second or more) bioactive compound may range between 1:1 and 1:10; 1:5 and 1:25; 1:10 and 1:50; 1:25 and 1:100; 1:50 and 1:500; or 1:100 and 1:1000.

Depending on the site of application and physiology of the subject, the amount of bioactive compound associated with the individual polymeric nanowires for administration to the subject may vary. In some instances, the amount of bioactive compound may range from 0.001 mg to 500 mg, such as 0.005 mg to 400 mg, such as 0.01 to 300 mg, such as 0.1 to 200 mg, such as 1 to 100 mg, such as 2 to 90 mg, such as 3 to 80 mg, such as 4 to 70 mg and including 5 mg to 50 mg. Alternatively, the amount of bioactive compound associated with the individual polymeric nanowires for administration to the subject may be a concentration (where the bioactive compound is present in a solvent), where the concentration may range, such as about 0.001-1000 $\mu M$, such as about 0.005-500 $\mu M$, such as about 0.01-100 $\mu M$, such as about 0.5-50 $\mu M$ and including 1 to 25 mM. As such, depending on the potency of the bioactive compound as well as the desired effect, the concentration of bioactive compounds delivered by the subject individual polymeric nanowires may range, from 0.01 $\mu M$ to 500 $\mu M$, such as 0.1 $\mu M$ to 250 $\mu M$, such as 0.1 $\mu M$ to 100 $\mu M$, such as 0.1 $\mu M$ to 75 $\mu M$, such as 0.1 $\mu M$ to 50 $\mu M$, such as 0.1 $\mu M$ to 25 $\mu M$, such as 0.1 $\mu M$ to 10 $\mu M$, and including 0.1 $\mu M$ to 1 $\mu M$.

Delivery of bioactive compound by the subject polymeric nanowires may vary, such as 0.5 $\mu g/cm^2/hr$ or greater, such as 0.6 $\mu g/cm^2/hr$ or greater, such as 0.65 $\mu g/cm^2/hr$ or greater, such as 0.75 $\mu g/cm^2/hr$, such as 0.9 $\mu g/cm^2/hr$, such as 1.0 $\mu g/cm^2/hr$ or greater, such as 1.5 $\mu g/cm^2/hr$ or greater, such as 1.75 $\mu g/cm^2/hr$ or greater and including peak flux of 2.0 $\mu g/cm^2/hr$ or greater.

In certain embodiments, compositions of individual polymeric nanowires having one or more bioactive compounds deliver bioactive compound at a substantially linear rate over a predetermined dosage interval (e.g., 1 day or longer). By "substantially linearly" is meant that the cumulative amount of bioactive compound released from the individual polymeric nanowires increases at a substantially constant rate (i.e., defined by first-order kinetics). As such, the change in rate of cumulatively delivered bioactive compound increases or decreases by 10% or less at any given time, such as 8% or less, such as 7% or less, such as 6% or less, such as 5% or less, such as 3% or less, such as 2.5% or less, such as 2% or less, and including 1% or less.

In other embodiments, compositions of individual polymeric nanowires having one or more bioactive compounds deliver an average cumulative amount of bioactive compound of 5 $\mu g/cm^2$ or greater over an extended period of time. The term "cumulative amount" is meant the total quantity of bioactive compound delivered by the individual polymeric nanowires in the composition. In these embodiments, compositions of individual polymeric nanowires of interest may be formulated to deliver an average cumulative amount of bioactive compound may be 25 $\mu g/cm^2$ or greater, such as 50 $\mu g/cm^2$ or greater, such as 75 $\mu g/cm^2$ or greater over a 4 week delivery interval, such as 100 $\mu g/cm^2$ or greater, such as 125 $\mu g/cm^2$ or greater, such as 150 $\mu g/cm^2$ or greater and including 200 $\mu g/cm^2$ over a predetermined delivery interval.

In yet other embodiments, compositions of individual polymeric nanowires having one or more bioactive compounds are formulated to deliver a target dosage of bioactive compound, such as for example as characterized by total bioactive compound exposure or by average daily bioactive compound exposure. The term target dosage is meant the amount of bioactive compound which is delivered to the subject and may vary depending on the physicochemical properties, mechanical properties, degradation rates of the individual polymeric nanowires as well as the site of administration. For example, the target dosage of bioactive compound delivered by the subject compositions may be 0.01 mg/day or greater, such as 0.04 mg/day or greater, such as 0.5 mg/day or greater over a 4 week dosage interval, such as 1.0 mg/day or greater, such as 2 mg/day or greater, such as 5 mg/day or greater and including 10 mg/day over a 4 week dosage interval.

Therefore, the dosage of bioactive compound delivered using the subject compositions of individual polymeric nanowires having one or more bioactive compounds t may vary, ranging from about 0.01 mg/kg to 500 mg/kg per day, such as from 0.01 mg/kg to 400 mg/kg per day, such as 0.01 mg/kg to 200 mg/kg per day, such as 0.1 mg/kg to 100 mg/kg per day, such as 0.01 mg/kg to 10 mg/kg per day, such as 0.01 mg/kg to 2 mg/kg per day, including 0.02 mg/kg to 2 mg/kg per day. In other embodiments, the dosage may range from 0.01 to 100 mg/kg four times per day (QID), such as 0.01 to 50 mg/kg QID, such as 0.01 mg/kg to 10 mg/kg QID, such as 0.01 mg/kg to 2 mg/kg QID, such as 0.01 to 0.2 mg/kg QID, depending on the dosage protocol as desired. In other embodiments, the dosage may range from 0.01 mg/kg to 50 mg/kg three times per day (TID), such as 0.01 mg/kg to 10 mg/kg TID, such as 0.01 mg/kg to 2 mg/kg TID, and including as 0.01 mg/kg to 0.2 mg/kg TID. In yet other embodiments, the dosage may range from 0.01 mg/kg to 100 mg/kg two times per day (BID), such as 0.01 mg/kg to 10 mg/kg BID, such as 0.01 mg/kg to 2 mg/kg BID, including 0.01 mg/kg to 0.2 mg/kg BID.

The polymeric nanowires described herein may be formed (as described in greater detail below) from one or more polymers. For example, individual polymeric nanowires may be formed from two or more different types of polymers, such as 3 or more different type of polymers, such as 4 or more different types of polymers and including 5 or more different types of polymers. Any suitable polymer may be employed in the subject methods, depending on the desired polymeric nanowire and may include, but is not limited to, polyesters, polycarbonates, polyvinyl chloride (PVC), polyurethanes, polyethers, polyamides, polyimides, or copolymers such as PETG (glycol-modified polyethylene terephthalate), among other polymeric materials. In certain embodiments, polymer compositions of interest include a polyester. The term "polyester" is used herein in it conventional sense to refer to the category of polymers which contains an ester functional group in their main chain. Polyesters of interest may be aliphatic polyesters such as polyglycolide (PGA), polylactide (PLA), polyethylene adipate (PEA), polyhydroxyalkanoate (PHA), polycaprolactone (PCL), polyhydroxybutyrate (PHB), poly(3-hydroxybutyrate-co-3-hydroxyvalerate)(PHBV) or aromatic polyesters such as polyethylene terephthalate (PET), polybutylene terephthalate (PBT), polytrimethylene terephthalate (PIT), polytrimethylene terephthalate (PTT) and polyethylene naphthalate (PEN), among other polyester polymers. In certain embodiments, the polymer composition is a polycaprolactone (PCL) composition. Depending on the type of polymer, the molecular weight of the polymer will vary ranging from 5 kDa to 500 kDa, such as from 10 kDa to 400 kDa, such as from 15 kDa to 300 kDa, such as from 20 kDa to 200 kDa, such as from 25 kDa to 150 kDa and including from 50 kDa to 100 kDa.

Individual polymeric nanowires having one or more bioactive compounds in the subject compositions may have aspect ratios of 2 or greater, such as 3 or greater, such as 4 or greater, such as 5 or greater, such as 6 or greater, such as 7 or greater, such as 8 or greater, such as 9 or greater and including 10 or greater. For example, the individual polymeric nanowires may have diameters that range from 10 nm to 500 nm, such as from 15 nm to 400 nm, such as from 20 nm to 300 nm, such as from 25 nm to 200 nm and including from 50 nm to 100 nm, such as a 200 nm diameter and have a length that is 0.01 µm or more, such as 0.05 µm or more, such as 0.1 µm or more, such as 0.5 µm or more, such as 1 µm or more, such as 2 µm or more, such as 3 µm or more, such as 5 µm or more, such as 10 µm or more, such as 15 µm or more, such as 20 µm or more, such as 25 µm or more, such as 30 µm or more, such as 50 µm or more, such as 100 µm or more, such as 150 µm or more, such as 200 µm or more and including 250 µm or more or more. In certain embodiments, individual polymeric nanowires having one or more bioactive compounds have a length of from 10 µm to 20 µm and a diameter of from 10 nm to 500 nm.

Compositions of interest may include one or more buffers. Example buffers may include but are not limited to PBS (phosphate) buffer, acetate buffer, N,N-bis(2-hydroxyethyl) glycine (Bicine) buffer, 3-{[tris(hydroxymethyl)methyl] amino}propanesulfonic acid (TAPS) buffer, 2-(N-morpholino)ethanesulfonic acid (MES) buffer, citrate buffer, tris(hydroxymethyl)methylamine (Tris) buffer, N-tris(hydroxymethyl)methylglycine (Tricine) buffer, 3-[N-Tris(hydroxymethyl)methylamino]-2-hydroxypropanesulfonic Acid (TAPSO) buffer, 4-2-hydroxyethyl-1-piperazineethanesulfonic acid (HEPES) buffer, 2-{[tris(hydroxymethyl)methyl]amino)ethanesulfonic acid (TES) buffer, piperazine-N,N'-bis(2-ethanesulfonic acid) (PIPES) buffer, dimethylarsinic acid (Cacodylate) buffer, saline sodium citrate (SSC) buffer, 2(R)-2-(methylamino)succinic acid (succinic acid) buffer, potassium phosphate buffer, N-Cyclohexyl-2-aminoethanesulfonic acid (CHES) buffer, among other types of buffered solutions.

In certain embodiments, compositions of individual polymeric nanowires having a bioactive compound may further include one or more pharmaceutically acceptable excipients as part of a pharmaceutical composition. Excipients may include, but are not limited to, carbohydrates, inorganic salts, antimicrobial agents, antioxidants, surfactants, buffers, acids, bases, and any combinations thereof. Excipients suitable for injectable compositions may include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may also be employed. Some carbohydrate excipients of interest include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. Inorganic salts may include, but are not limited to citric acid, sodium chloride, potassium chloride, sodium sulfate, potassium nitrate, sodium phosphate monobasic, sodium phosphate dibasic, and any combinations thereof.

In certain embodiments, compositions of individual polymeric nanowires having a bioactive compound may also include an antimicrobial agent for preventing or deterring microbial growth, such as for example benzalkonium chloride, benzethonium chloride, benzyl alcohol, cetylpyridinium chloride, chlorobutanol, phenol, phenylethyl alcohol, phenylmercuric nitrate, thimersol, and any combinations thereof.

One or more antioxidants may also be employed. Antioxidants, which can reduce or prevent oxidation and thus deterioration of the composition, may include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and any combinations thereof.

One or more surfactants may also be included in the subject compositions of individual polymeric nanowires having a bioactive compound. For example, suitable surfactants may include, but are not limited to polysorbates, such as "Tween 20" and "Tween 80," and pluronics such as F68 and F88 (BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other cations.

Acids or bases may also be present. For example, acids may include but are not limited to hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and any combinations thereof. Examples bases include, but are not limited to sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and any combinations thereof.

The amount of any individual excipient in the subject compositions will vary depending on the nature and function of the. Generally, the excipient(s) will be present in the composition in an amount of about 1% to about 99% by weight, such as from about 5% to about 98% by weight, such as from about 15 to about 95% by weight of the excipient, including less than 30% by weight. Pharmaceutical excipients along with other excipients that may be employed in compositions of the invention are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000, the disclosure of which is herein incorporated by reference.

As described in greater detail below, compositions of individual polymeric nanowires having a bioactive compound may be administered by any convenient mode of administration. As such, the formulation may vary. For example, compositions of the invention may be an injection, such as injection solutions or suspensions, dry insoluble compositions for combination with a vehicle prior to use, and emulsions and liquid concentrates for dilution prior to administration. In embodiments where compositions of the invention are employed for injections, diluents may include, but is not limited to bacteriostatic water for injection, dextrose 5% in water, phosphate buffered saline, Ringers solution, saline, sterile water, deionized water, and any combinations thereof.

Compositions of individual polymeric nanowires having a bioactive compound may be pre-loaded into a syringe, an implantation device, or the like, depending upon the intended mode of delivery and use. In certain embodiments, the compositions are in unit dosage form, such that an amount of the composition is ready in a single dose, in a premeasured or pre-packaged form.

Methods for Preparing Compositions of Individual Polymeric Nanowires

As summarized above, aspects of the present disclosure include methods for preparing compositions of individual polymeric nanowires. By "individual polymeric nanowires" is meant a composition that include; discrete, free-floating polymeric nanowires which are not joined together, such as being attached to a substrate. In other words, the subject polymeric nanowires are individualized structures and are not connected to each other or bonded to a common substrate. As described in greater detail below, the individual polymeric nanowires are formed in a vertical array of parallel pores of a template structure and are removed so that there is no permanent (e.g., covalent bond) between each polymeric nanowire or a bond between the polymeric nanowires and a substrate.

Individual polymeric nanowires prepared by the subject methods, as described below, have aspect ratios of 2 or greater, such as 3 or greater, such as 4 or greater, such as 5 or greater, such as 6 or greater, such as 7 or greater, such as 8 or greater, such as 9 or greater and including 10 or greater. For example, the subject methods may be employed to prepare individual, free-floating nanowires having diameters with range from 10 nm to 500 nm, such as from 15 nm to 400 nm, such as from 20 nm to 300 nm, such as from 25 nm to 200 nm and including from 50 nm to 100 nm. In certain embodiments, individual, free-floating nanowires prepared by the subject methods have a 200 nm diameter. The subject methods may be employed to prepare individual, free-floating nanowires having a length that is 0.01 µm or more, such as 0.05 µm or more, such as 0.1 µm or more, such as 0.5 µm or more, such as 1 µm or more, such as 2 µm or more, such as 3 µm or more, such as 5 µm or more, such as 10 µm or more, such as 15 µm or more, such as 20 µm or more, such as 25 µm or more, such as 30 µm or more, such as 50 µm or more, such as 100 µm or more, such as 150 µm or more, such as 200 µm or more and including 250 µm or more or more. In certain embodiments, the subject methods may be employed to prepare individual, free-floating nanowires having a length of from 10 µm to 20 µm and a diameter of from 10 nm to 500 nm.

In practicing the subject methods, a polymer composition is applied to the surface of a substrate to produce a polymer-coated substrate. As used herein, the term "applying" refers to placing the polymer composition onto a surface, such as for example onto the surface of a substrate. As such, applying may include positioning on top, depositing or otherwise producing the polymer composition on a surface of a substrate. For example, the polymer composition may be deposited onto the substrate surface by spraying, brushing, painting, drop-casting, spin-coating, spreading with a blade, draw casting, sputtering or other convenient protocol.

Depending on the desired properties of the polymeric nanowires, the polymer composition may include one or more polymers as desired. In some embodiments, the polymer composition includes a single type of polymer and the polymeric nanowires are composed of a single type of polymer. In other embodiments, the polymer composition includes two or more different types of polymers, such as 3 or more different type of polymers, such as 4 or more different types of polymers and including 5 or more different types of polymers.

Any suitable polymer may be employed in the subject methods, depending on the desired polymeric nanowire and may include, but is not limited to, polyesters, polycarbonates, polyvinyl chloride (PVC), polyurethanes, polyethers, polyamides, polyimides, or copolymers such as PETG (glycol-modified polyethylene terephthalate), among other polymeric materials. In certain embodiments, polymer compositions of interest include a polyester. The term "polyester" is used herein in it conventional sense to refer to the category of polymers which contains an ester functional group in their main chain. Polyesters of interest may be aliphatic polyesters such as polyglycolide (PGA), polylactide (PLA), polyethylene adipate (PEA), polyhydroxyalkanoate (PHA), polycaprolactone (PCL), polyhydroxybutyrate (PHB), poly(3-hydroxybutyrate-co-3-hydroxyvalerate)(PHBV) or aromatic polyesters such as polyethylene terephthalate (PET), polybutylene terephthalate (PBT), polytrimethylene terephthalate (PI), polytrimethylene terephthalate (PTT) and polyethylene naphthalate (PEN), among other polyester polymers. In certain embodiments, the polymer composition is a polycaprolactone (PCL) composition. Depending on the type of polymer, the molecular weight of the polymer will vary ranging from 5 kDa to 500 kDa, such as from 10 kDa to 400 kDa, such as from 15 kDa to 300 kDa, such as from 20 kDa to 200 kDa, such as from 25 kDa to 150 kDa and including from 50 kDa to 100 kDa.

In some embodiments, the polymer composition includes a solvent. Any solvent may be employed so long as the solvent is compatible with the one or more polymers in the polymer composition and can be removed (as described in greater detail below) after application of the polymer composition to the substrate surface. For example, the solvent may be water, an alcohol such as methanol, ethanol, propanol, butanol, pentanol, hexanol or octanol or another type of alcohol including trifluoroethanol, an ether such as diethyl ether or tetrahydrofuran, an acetate such as ethyl acetate, a halogenated solvent such as dichloromethane or chloroform, aromatic solvents such as benzene, xylenes or toluene, acetone, or a hydrocarbon solvent such as pentane or hexanes. The concentration of the polymer in the solvent in polymer compositions of interest may vary and may be 1 mg/mL or more, such as 5 mg/mL or more, such as 10 mg/mL or more, such as 25 mg/mL or more, such as 50 mg/mL or more, such as 75 mg/mL or more, such as 100 mg/mL or more, such as 125 mg/mL or more, such as 150 mg/mL or more, such as 250 mg/mL or more, such as 500 mg/mL or more and including 750 mg/mL or more. In some embodiments, the concentration of polymer in the polymer composition ranges from 1 mg/mL to 1000 mg/mL, such as from 2 mg/mL to 750 mg/mL, such as from 3 mg/mL to 500 mg/mL, such as from 4 mg/mL to 400 mg/mL and including from 5 mg/mL to 250 mg/mL. In other embodiments, the polymer concentration is 0.0005 μM or more, such as 0.001 μM or more, such as 0.005 μM or more, such as 0.01 μM or more, such as 0.05 μM or more, such as 0.1 μM or more, such as 0.5 μM or more, such as 1 μM or more, such as 2 μM or more, such as 5 μM or more, such as 10 μM or more, such as 50 μM or more, such as 100 μM or more, such as 500 μM or more and including 1 mM or more, such as 5 mM or more, such as 10 mM or more, such as 25 mM or more, such as 50 mM or more and including 100 mM or more. As such, the polymer concentration in the polymer composition applied to the substrate surface may range from 0.0005 μM to 500 mM, such as from 0.001 μM to 100 mM, such as from 0.005 μM to 10 mM and including from 0.01 μM to 1 mM.

In certain embodiments, applying includes depositing a layer of the polymer composition onto a surface of the substrate. For example, methods may include depositing a thin layer of the polymer composition onto the surface of the substrate, such as layer having a thickness of 0.001 μm or more, such as 0.005 μm or more, such as 0.01 μm or more, such as 0.05 μm or more, such as 0.1 μm or more, such as 0.5 μm or more, such as 1 μm or more, such as 2 μm or more, such as 3 μm or more, such as 5 μm or more, such as 10 μm or more, such as 15 μm or more, such as 20 μm or more, such as 25 μm or more, such as 30 μm or more and including 50 μm or more. In embodiments, the polymer composition may be applied over the entire surface or a part of the surface of the substrate, as desired. In some embodiments, applying the polymer composition to the substrate surface includes depositing the polymer composition onto less than the entire substrate surface. For instance, applying the polymer composition to the substrate surface may include depositing the polymer composition onto 50% or less of the entire substrate surface, such as 40% or less, such as 25% or less, such as 10% or less, such as 5% or less and including 1% or less of the entire substrate surface. In certain instances, applying the polymer composition to the substrate surface includes depositing the polymer composition to specific locations on the substrate surface. For example, depositing the polymer composition to specific locations may include depositing the polymer composition onto the substrate surface in the form of spots (or any other geometric shape) or strips (e.g., straight or non-straight having regular and irregular patterns).

The thickness of the applied polymer composition will depend on the polymer, the rate of deposition, the number of layers applied and the duration of deposition. In some embodiments, the rate of deposition may range, such as from 0.01 to 500 μm/s, such as 0.1 to 250 μm/s, such as 1 to 100 μm/s, such as 10 to 90 μm/s, such as 15 to 75 μm/s, such as 20 to 60 μm/s, including 25 to 50 μm/s. The polymer composition may be applied to the substrate surface for 0.5 seconds or longer, such as 1 second or longer, such as 2 seconds or longer, such as 5 seconds or longer, such as 10 seconds or longer, such as 30 seconds or longer, including 60 seconds or longer. One or more layers of the polymer composition may be applied to the substrate surface. For example, two or more layers of the polymer composition may be applied to the substrate surface, such as three or more layers, such as four or more layers, including 5 or more layers of the polymer composition may be applied to the substrate surface. As described in greater detail below, additional layers of the polymer composition may be added if necessary, such as for example to improve smoothness and uniformity of the polymer composition. For example, if after evaluating the deposited the applied polymer composition, it is determined that the polymer composition is less than optimal or is unsuitable, additional layers of the polymer composition may be applied to all or part of the deposited polymer composition. As such, the thickness of the final deposited polymer composition may be 0.001 μm or more, such as 0.005 μm or more, such as 0.01 μm or more, such as 0.05 μm or more, such as 0.1 μm or more, such as 0.5 μm or more, such as 1 μm or more, such as 2 μm or more, such as 3 μm or more, such as 5 μm or more, such as 10 μm or more, such as 15 μm or more, such as 20 μm or more, such as 25 μm or more, such as 30 μm or more and including 50 μm or more. The amount of deposited polymer material will vary depending on the size of the applied area on the substrate as well as the number of layers deposited. In certain instances, the amount of polymer applied to the substrate surface is 1 mg or more, such as 2 mg or more, such as 5 mg or more, such as 10 mg or more, such as 15 mg or more, such as 25 mg or more, such as 50 mg or more, such as 75 mg or more, such as 100 mg or more, such as 125 mg or more, such as 150 mg or more, such as 250 mg or more, such as 500 mg or more, such as 750 mg or more, such as 1000 mg or more, such as 1500 mg or more, such as 2000 mg or more, such as 5000 mg or more and including 10000 mg or more.

In some embodiments, the substrate is moved while applying the polymer composition. By "moved" is meant that movement is applied to the substrate in a regular pattern during application of the polymer composition. For example, the substrate may be rotated while the polymer composition is applied. In other instances, lateral movement may be applied to the substrate during application of the polymer composition.

In certain instances, the substrate is rotated during application of the polymer composition. For example, the substrate may be rotated continuously during application. By "rotated continuously" is meant that the substrate rotates either clockwise or counterclockwise without a change in direction at any time during application of the polymer composition. For example, the substrate may be rotated continuously in a clockwise direction as the polymer composition is deposited. In other instances, the substrate is rotated continuously in a counterclockwise direction as the polymer composition is deposited. The rotation rate of the substrate while the polymer composition is deposited may vary, ranging from $1\times10^{-3}$ to $1\times10^{5}$ rps (revolutions per second), such as from $5\times10^{-2}$ to $1\times10^{5}$ rps, such as from $1\times10^{-2}$ to $5\times10^{4}$ rps, such as from $5\times10^{-1}$ to $1\times10^{3}$ rps, such as 1 to $5\times10^{2}$ rps, including 5 to 10 rps. Any convenient protocol can be used to rotate the substrate while depositing the polymer composition, such as for example by an electric motor, an electromagnetic rotation device, among others.

In other instances, the substrate may be rotated in a reciprocating motion. By "reciprocating motion" is meant the substrate is rotated in an alternating fashion such that the substrate rotates in one direction (e.g., clockwise) for a first predetermined period of time and changes direction to rotate in the opposing direction (e.g., counterclockwise) for second predetermined period of time. For example, the substrate may be rotated in a "back-and-forth" motion, alternating between clockwise and counterclockwise motion. Each direction (e.g., clockwise or counterclockwise) can be performed for any amount of time as desired. For example, the substrate may be rotated in either direction for $10^{3}$ seconds or more, such as $10^{-2}$ seconds or more, such as $10^{-1}$ seconds or more, such as 1 second or more, such as 2 seconds or more, such as 5 seconds or more, such as 10 seconds or more, such as 100 seconds or more, including 500 seconds or more. The rate of rotation in either direction may be the same or different, as desired. The rate of rotation in either direction may be constant (i.e., stays the same throughout application of the polymer composition) or may be variable (i.e., changes at any time during application of the polymer composition). Furthermore, the reciprocating motion may be repeated as desired, such as 2 times or more, such as 5 times or more, such as 10 times or more, such as 50 times or more, such as 100 times or more, such as 1000 times or more, such as 10,000 times or more, including 100,000 times or more.

In other embodiments, lateral movement is applied to the substrate while the polymer composition is deposited. By "lateral movement" is meant the substrate is moved in a back and forth motion such that a particular location on the substrate may move a predetermined distance, come to a stop and return to its original location. Lateral movement can be made in any direction, such as vertically, horizontally, or any combination thereof (i.e., diagonally with respect to the midline of the substrate). The amplitude or total displacement of the substrate may vary. By "amplitude of displacement" or "total displacement" is meant the sum total of distance traversed by a particular location (e.g., midline) on the substrate during movement. For example, lateral movement applied to a substrate which has a total displacement of 2 mm is meant the location traverses a total of 2 mm during the lateral movement. For example, the location may move 2 mm from the initial location and come to a stop resulting in a 2 mm total displacement or the location may move 1 mm from the initial location and move a second 1 mm to return to its initial location. In embodiments of the present disclosure, lateral movement of the substrate when applying the polymer composition may vary, the amplitude of displacement ranging from about 10 to 50 mm, such as from about 15 to 45 mm, such as from about 15 to 40 mm, such as from about 15 to 35, such as from about 20 to 30 mm, including from about 22 to 25 mm. The rate of lateral movement may vary. For example, the back and forth movement of the substrate may range from about 1 to 25 times per second, such as 5 to 25 times per second, such as 10 to 20 times per second, including 15 times per second.

The temperature of the substrate during application of the polymer composition may vary, ranging such as from 0° C. to 250° C., such as from 10° C. to 200° C., such as from 15° C. to 150° C., such as from 25° C. to 100° C., including 30° C. to 50° C. In certain instances, the temperature of the substrate is not changed and remains at room temperature throughout the entire deposition process. If desired, the temperature of the substrate may be modified at any time during the deposition of the polymer composition. In other words, the temperature of the substrate may be increased or decreased at any time while the polymer composition is deposited to the substrate. As such, the temperature of the substrate may be increased or decreased by 0.01° C. or more, such as 0.05° C. or more, such as 0.1° C. or more, such as 0.5° C. or more, such as 1° C. or more, such as 5° C. or more, such as 10° C. or more, such as 25° C. or more, such as 50° C. or more, such as 100° C. or more, including 250° C. or more. The temperature may also be maintained at a constant temperature. The temperature of the substrate may be modified by any convenient protocol, so long as it can cool or heat the substrate and may include but is not limited to thermal heat exchangers, electric heating coils, Peltier thermoelectric devices, coils employing refrigerants, coils employing cryogenic fluids, among other protocols.

In embodiments, the polymer composition may be applied to the substrate under atmospheric pressure or under positive or reduced pressure. By "reduced pressure" is meant that the polymer composition is deposited onto the substrate at a pressure below atmospheric pressure. For example, the polymer composition may be applied at a pressure of $10^{-2}$ torr or lower, such as $10^{-3}$, such as $10^{-4}$ torr or lower, such as $10^{-5}$ torr or lower and including $10^{-6}$ torr or lower. In certain instances, the polymer composition is deposited under a high vacuum. By "high vacuum" is meant that the polymer composition is applied to the substrate at very low pressures, such as $10^{-7}$ torr or lower, such as $10^{-8}$ torr or lower and including $10^{-10}$ torr or lower. By "positive pressure is meant that the polymer composition is deposited onto the substrate at a pressure above atmospheric pressure. For example, the polymer composition may be applied at a pressure that is 1 torr or more above atmospheric pressure, such as 5 torr or more, such as 10 torr or more, such as 25 torr or more, such as 50 torr or more, such as 75 torr or more, such as 100 torr or more, such as 250 torr or more, such as 500 torr or more, such as 750 torr or more and including 1500 torr or more above atmospheric pressure.

In practicing the subject methods, the polymer composition may be applied to a substrate that is formed from any suitable material including, but not limited to metal, glass, ceramic, or plastic. In some embodiments, the substrate is a glass substrate. In other embodiments, the substrate is a ceramic substrate. In yet other embodiments, the substrate is formed from a metal, such as aluminum, chromium, cobalt, copper, gold, indium, iron, lead, nickel, tin, steel (e.g., stainless steel), silver, zinc and combinations and alloys thereof. In still other embodiments, the substrate is a plastic substrate, such as a rigid plastic, polymeric or thermoplastic material. For example, suitable plastics may include polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials. In certain embodiments, the substrate is formed from a polyester, where polyesters of interest may include, but are not limited to poly(alkylene terephthalates) such as poly (ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate)(PBT), and poly(hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(ε-caprolactone) and poly(O-propiolactone); poly(alkylene isophthalates) such as poly(ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly (trans-1,4-cyclohexanediyl ethylene dicarboxylate); poly(1, 4-cyclohexane-dimethylenealkylene dicarboxylates) such as poly(1,4-cyclohexane-dimethyleneethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly (tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p-phenylene terephthalamide); Mylar™.

Applying the polymer composition to the substrate surface produces a polymer-coated substrate. In some embodiments, methods also include processing the polymer-coated substrate before positioning the template structure on the polymer-coated substrate. In certain instances, processing the polymer-coated substrate includes removing solvent from the applied polymer composition. The solvent may be removed by any convenient protocol, such as by heating the polymer-coated substrate, subjecting the polymer-coated substrate to reduced pressure to remove the solvent or a combination thereof. In some embodiments, methods include heating the polymer-coated substrate. To remove solvent, the temperature of the substrate may be increased or decreased by 0.01° C. or more, such as 0.05° C. or more, such as 0.1° C. or more, such as 0.5° C. or more, such as 1° C. or more, such as 5° C. or more, such as 10° C. or more, such as 25° C. or more, such as 50° C. or more, such as 100° C. or more, including 250° C. or more. The temperature of the substrate may be modified by any convenient protocol, including but is not limited to a heat gun, oven, thermal heat exchangers, electric heating coils, Peltier thermoelectric devices, among other protocols. In these embodiments, the temperature of the polymer-coated substrate may be increased from 5° C. to 250° C., such as from 10° C. to 200° C., such as from 15° C. to 150° C., such as from 25° C. to 100° C. and including 30° C. to 50° C. to remove solvent from the applied polymer composition. In other embodiments, to remove solvent the polymer-coated substrate may be subjected to reduced pressure, such as a pressure of $10^{-2}$ torr or lower, such as $10^{-3}$, such as $10^{-4}$ torr or lower, such as $10^{-5}$ torr or lower, such as $10^{-6}$ torr or lower, such as $10^{-7}$ torr or lower, such as $10^{-8}$ torr or lower and including $10^{-10}$ torr or lower.

Before positioning the template structure onto the polymer-coated substrate, the polymer-coated composition may be heated. In some embodiments, methods include heating the polymer-coated substrate to a temperature above the melting temperature of the polymer, such as from 5° C. to 100° C. above the melting temperature of the polymer, such as from 10° C. to 90° C. above the melting temperature of the polymer, such as from 15° C. to 80° C. above the melting temperature of the polymer, such as from 20° C. to 75° C. above the melting temperature of the polymer, such as from 25° C. to 70° C. above the melting temperature of the polymer and including from 30° C. to 60° C. above the melting temperature of the polymer. By heating the polymer-coated substrate to a temperature above the melting temperature of the polymer, the polymer on the substrate surface become molten and flowable.

After heating the polymer-coated substrate (such as to make the polymer molten and flowable), the template structure is positioned on the polymer-coated substrate and maintained in contact with the polymer-coated substrate in a manner sufficient to draw polymer into the pores of the template structure. The template structure may be positioned onto the polymer-coated substrate immediately after heating the polymer composition on the substrate surface or may be positioned after a predetermined period of time. In certain embodiments, the template structure is applied immediately after heating the polymer-coated substrate (e.g., after forming molten polymer on the substrate surface). In other embodiments, the template structure is applied after 1 second or more, such as 2 seconds or more, such as 3 seconds or more, such as 5 seconds or more, such as 10 seconds or more, such as 30 seconds or more and including after 60 seconds or more after heating the polymer-coated substrate (e.g., after forming molten polymer on the substrate surface).

The template structure may be any suitable porous material having a vertical array of pores. For example, the template structure may be a porous metal, a ceramic, a glass, a track etched memembrane or a plastic (e.g., thermoplastic material). For example, suitable plastics may include polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials. In some embodiments, the template structure is a porous metal oxide including porous oxides of aluminum, chromium, cobalt, copper, gold, indium, iron, lead, nickel, tin, steel (e.g., stainless steel), silver, zinc and combinations thereof. In certain embodiments, the template structure is a porous aluminum oxide (e.g., Anapore).

Depending on the dimensions of the polymeric nanowires desired, the pore sizes of the template structure will vary. In some embodiments, the diameter of the pores of the template structure ranges from 10 nm to 500 nm, such as from 15 nm to 400 nm, such as from 20 nm to 300 nm, such as from 25 nm to 200 nm and including from 50 nm to 100 nm. In certain embodiments, the template structure has 200 nm pores. The length of the pores in the template also varies and may be 0.01 µm or more, such as 0.05 µm or more, such as 0.1 µm or more, such as 0.5 µm or more, such as 1 µm or more, such as 2 µm or more, such as 3 µm or more, such as 5 µm or more, such as 10 µm or more, such as 15 µm or more, such as 20 µm or more, such as 25 µm or more, such as 30 µm or more, such as 50 µm or more, such as 100 µm or more, such as 150 µm or more, such as 200 µm or more and including 250 µm or more or more.

The cross-sectional shape of the pores may vary depending on the desired cross-sectional shape of the formed polymeric nanowires. In embodiments, the cross-sectional shape of the pores may be a circle, a semi-circle, oval, moon-shaped, crescent shaped, polygonal or other shape or a combination thereof. In some embodiments the cross-sectional shape of the pores of the template structure is a circle. In other embodiments, the cross-sectional shape of the pores of the template structure is polygonal, e.g., square, rectangle, pentagon, hexagon, octagon or some other polygon. In still other embodiments, the cross-sectional shape of the pores of the template structure is oval.

As described above, the template structure is maintained in contact with the polymer-coated substrate to draw the polymer (e.g., molten polymer) into the pores of the template structure. The template structure may be maintained to draw the polymer into the pores for a duration of 1 minute or more, such as 5 minutes or more, such as 10 minutes or more, such as 15 minutes or more, such as 30 minutes or more, such as 60 minutes or more, such as 90 minutes or more, such as 120 minutes or more, such as 150 minutes or more, such as 180 minutes or more, such as 210 minutes or more, such as 240 minutes or more, such as 300 minutes or more, such as 360 minutes or more and including 500 minutes or more. In certain embodiments, the template structure is maintained in contact with the polymer coated substrate until all of the polymer from the substrate is drawn up into the pores of the template and the template structure is in direct contact with the substrate surface. In these embodiments, the template structure is directly touching the uncoated substrate surface and substantially all of the polymer coating is drawn up into the pores of the template.

The temperature while maintaining the template structure in contact with the polymer-coated substrate may vary, ranging such as from 0° C. to 250° C., such as from 10° C. to 200° C., such as from 15° C. to 150° C., such as from 25° C. to 100° C., including 30° C. to 50° C. In certain embodiments, the temperature is not changed and remains at room temperature while drawing the polymer into the pores of the template structure. If desired, the temperature may be modified at any time. In other words, the temperature may be increased or decreased. As such, the temperature may be increased or decreased by 0.01° C. or more, such as 0.05° C. or more, such as 0.1° C. or more, such as 0.5° C. or more, such as 1° C. or more, such as 5° C. or more, such as 10° C. or more, such as 25° C. or more, such as 50° C. or more, such as 100° C. or more, including 250° C. or more. The temperature may be modified by any convenient protocol, so long as it can cool or heat the substrate and may include but is not limited to thermal heat exchangers, electric heating coils, Peltier thermoelectric devices, coils employing refrigerants, coils employing cryogenic fluids, among other protocols.

Pressure may be applied to draw the polymer into the pores of the template structure. In some embodiments, a pressure of 1 psi or more is applied, such as 5 psi or more, such as 10 psi or more, such as 25 psi or more, such as 50 psi or more, such as 75 psi or more, such as 100 psi or more, such as 250 psi or more, such as 500 psi or more, such as 750 psi or more, such as 1000 psi and including applying a pressure of 1500 psi. For example, the pressure applied may range from 1 psi to 1000 psi, such as from 2 psi to 900 psi, such as from 3 psi to 800 psi, such as from 4 psi to 700 psi, such as from 5 psi to 600 psi, such as from 6 psi to 500 psi, such as from 7 psi to 400 psi, such as from 8 psi to 300 psi, such as from 9 psi to 200 psi and including from 10 psi to 100 psi.

In practicing the subject methods, the produced polymeric nanowires are removed from the template. In some embodiments, the polymeric nanowires are removed by breaking up the template and etching the template. In certain instances, the template structure is etched with a base. In other instances, the polymeric nanowires are removed by breaking up the template into a plurality of pieces and dissolving in a base. Any convenient base may be employed which is will etch or dissolve the template structure and is compatible with the polymer used to form the nanowires. In some embodiments, the base is a hydroxide base, such as a potassium hydroxide, calcium hydroxide, sodium hydroxide or ammonium hydroxide. In other instances, the template structure is etched with an acid. In yet other instances, the template structure is etched by differential solvation, such as where the template and the polymeric nanowires are solvated by different solvents and a solvent that does not dissolve the polymeric nanowires, but does dissolve the template structure is used to remove the template structure from the polymeric nanowires. In yet other instances, the polymeric nanowires are removed by breaking up the template into a plurality of pieces and dissolving in an acid. Any convenient acid may be employed which will etch or dissolve the template structure and is compatible with the polymer used to form the nanowires. In some embodiments, the acid is selected from the group consisting of phosphoric acid, nitric acid, sulfuric acid, hydrochloric acid and hydrogen peroxide.

The template with formed polymeric nanowires is contacted with the base (e.g., dissolved in base) for a duration sufficient to release the polymeric nanowires into the base solution. For example, the template with formed polymeric nanowires may be contacted with the base (e.g., dissolved in base) for a duration of 1 minute or more, such as 5 minutes or more, such as 10 minutes or more, such as 15 minutes or more, such as 30 minutes or more, such as 60 minutes or more, such as 90 minutes or more, such as 120 minutes or more, such as 150 minutes or more, such as 180 minutes or more, such as 210 minutes or more, such as 240 minutes or more, such as 300 minutes or more, such as 360 minutes or more and including 500 minutes or more. In certain embodiments, the template with formed polymeric nanowires is shaken, vortexed or sonicated while in the base to further release the polymeric nanowires into solution.

After the produced polymeric nanowires are released from the template structure, the solution of individual, free-floating polymeric nanowires may be further purified. In some embodiments, purifying includes neutralizing any residual base in the solution and filtering the polymeric nanowires with deionized water. Any number of purification cycles may be conducted until the desired purity of individual, free-floating nanowires is achieved. In certain embodiments, purifying includes sonicating the solution of individualized, free-floating nanowires. In some embodiments, purifying include centrifuging the solution of individualized, free-floating nanowires.

FIG. 1 depicts preparing a composition having individual, free-floating polymeric nanowires according to certain embodiments of the present disclosure. At step 1, a layer of a polymer composition having a polymer (e.g., polycaprolactone) in solvent is spin coated onto the surface of a glass substrate. After heating the polymer-coated substrate (e.g. baking at 110° C. for 1 minute), a porous aluminum oxide template structure is applied to the polymer-coated substrate (step 2). Heat is applied to a temperature above the melting point of the polymer to form molten polymer which is drawn into the pores of the porous aluminum oxide template. After substantially all of the polymer is drawn into the porous aluminum oxide template structure and the template structure comes into direct contact with the substrate surface (step 3), the template is removed by etching with strong sodium hydroxide base. The basic solution is neutralized (step 4) and the individualized, free-floating polymeric nanowires are collected and neutralized (step 5). To purify the nanowire composition, the solution is sonicated, strained and washed with deionized water (step 6).

In certain embodiments, methods further include contacting the composition of individual polymeric nanowires with a bioactive compound to produce a composition of individual polymeric nanowires incorporating a bioactive agent. As discussed above, any desired bioactive compound may be combined with the individual polymeric nanowires described herein and may include, but is not limited to interferon, interloukin, erythropoietin, granulocyte-colony stimulating factor (GCSF), stem cell factor (SCI:), leptin (OB protein), interferon (alpha, beta, gamma), antibiotics such as vancomycin, gentamicin ciprofloxacin, amoxycillin, lactobacillus, cefotaxime, levofloxacin, cefipime, mebendazole, ampicillin, lactobacillus, cloxacillin, norfloxacin, tinidazole, cefpodoxime, proxctil, azithromycin, gatifloxacin, roxithromycin, cephalosporin, anti-thrombogenics, aspirin, ticlopidine, sulfinpyrazone, heparin, warfarin, growth factors, differentiation factors, hepatocyte stimulating factor, plasmacytoma growth factor, glial derived neurotrophic factor (GDNF), neurotrophic factor 3 (NT3), fibroblast growth factor (FGF), transforming growth factor (TGF), platelet transforming growth factor, milk growth factor, endothelial growth factors, endothelial cell-derived growth factors (ECDGF), alpha-endothelial growth factors, beta-endothelial growth factor, neurotrophic growth factor, nerve growth factor (NGF), vascular endothelial growth factor (VEGF), 4-1 BB receptor (4-IBBR), TRAIL (TNF-related apoptosis inducing ligand), artemin (GFRalpha3-RET ligand), BCA-I (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, thrombopoietin, megakaryocyte derived growth factor (MDGF), keratinocyte growth factor (KGF), platelet-derived growth factor (PDGF), ciliary neurotrophic factor (CNTF), neurotrophin 4 (NT4), granulocyte colony-stimulating factor (GCSF), macrophage colony-stimulating factor (mCSF), bone morphogenetic protein 2 (BMP2), BRAK, C-IO, Cardiotrophin 1 (CT1), CCR8, anti-inflammatory: paracetamol, salsalate, diflunisal, mefenamic acid, diclofenac, piroxicam, ketoprofen, dipyrone, acetylsalicylic acid, anti-cancer drugs such as aliteretinoin, altertamine, anastrozole, azathioprine, bicalutarnide, busulfan, capecitabine, carboplatin, cisplatin, cyclophosphamide, cytarabine, doxorubicin, epirubicin, etoposide, exemestane, vincristine, vinorelbine, hormones, thyroid stimulating hormone (TSH), sex hormone binding globulin (SHBG), prolactin, luteotropic hormone (LTH), lactogenic hormone, parathyroid hormone (PTH), melanin concentrating hormone (MCH), luteinizing hormone (LHb), growth hormone (HGH), follicle stimulating hormone (FSHb), haloperidol, indomethacin, doxorubicin, epirubicin, amphotericin B, Taxol, cyclophosphamide, cisplatin, methotrexate, pyrene, amphotericin B, anti-dyskinesia agents, Alzheimer vaccine, antiparkinson agents, ions, edetic acid, nutrients, glucocorticoids, heparin, anticoagulation agents, antivirus agents, anti-HIV agents, polyamine, histamine and derivatives thereof, cystineamine and derivatives thereof, diphenhydramine and derivatives, orphenadrine and derivatives, muscarinic antagonist, phenoxybenzamine and derivatives thereof, protein A, streptavidin, amino acid, beta-galactosidase, methylene blue, protein kinases, beta-amyloid, lipopolysaccharides, eukaryotic initiation factor-4G, tumor necrosis factor (TNF), tumor necrosis factor-binding protein (TNF-bp), interleukin-1 (to 18) receptor antagonist (IL-Ira), granulocyte macrophage colony stimulating factor (GM-CSF), novel erythropoiesis stimulating protein (NESP), thrombopoietin, tissue plasminogen activator (TPA), urokinase, streptokinase, kallikrein, insulin, steroid, acetaminophen, analgesics, antitumor preparations, anti-cancer preparations, anti-proliferative preparations or pro-apoptotic preparations, among other types of bioactive agents.

The bioactive compounds may be absorbed into pores of the polymeric nanowires or may be affixed to a surface of the polymeric nanowire, such as by non-covalent interactions (e.g., ionic forces, dipole-dipole interactions, hydrogen bonding) or by one or more covalent bonds. In some embodiments, the bioactive compounds are contained within pores of the polymeric nanowires. The bioactive compound may be introduced into the pores of the polymeric nanowires by any convenient protocol. In certain embodiments, as described in greater detail below, the one or more bioactive compounds are incorporated into the polymeric nanowires by incubating the individual polymeric nanowires in the presence of the one or more bioactive compounds with or without a solvent for a predetermined amount of time, such as for 1 hour or more, 5 hours or more, 10 hours or more, 12 hours or more, 24 hours or more, 3 days or more and including 1 week or more, to allow the polymeric nanowires to incorporate one of more bioactive compounds into the pores of the polymeric nanowire.

In some embodiments, the one or more bioactive compounds may be added directly to the basic component mixture of the polymeric nanowires such that during fabrication such that the one or more bioactive compounds may be incorporated into the final individual polymeric nanowires.

In other embodiments, the bioactive compound is covalently bonded to each individual polymeric nanowire. In some instances, the bioactive compound is directly bonded to the polymeric nanowire (e.g., to the outer surface of the nanowire). In other instances, the bioactive compound is bonded to the polymeric nanowire through a linker. The bioactive compound may be covalently bonded to the polymer nanowire by any convenient protocol, including but not limited to addition reactions, elimination reactions, substitution reactions, pericyclic reactions, photochemical reactions, redox reactions, radical reactions, reactions through a carbene intermediate, metathesis reaction, among other types of bond-forming reactions. In some embodiments, the bioactive compound is covalently bonded to the polymeric nanowire through reactive linking chemistry such as where reactive linker pairs include, but is not limited to: maleimide/thiol; maleimide/alcohol; thiol/thiol; pyridyldithiol/thiol; succinimidyl iodoacetate/thiol; N-succinimidylester (NHS ester), sulfodicholorphenol ester (SDP ester), or pentafluorophenyl-ester (PFP ester)/amine; bissuccinimidy-lester/amine; imidoesters/amines; hydrazine or amine/aldehyde, dialdehyde or benzaldehyde; isocyanate/hydroxyl or amine; carbohydrate-periodate/hydrazine or amine; diazirine/aryl azide chemistry; pyridyldithiol/aryl azide chemistry; alkyne/azide; carboxy-carbodiimide/amine; amine/Sulfo-SMCC (Sulfosuccinimidyl 4-[N-maleimidomethyl]cyclohexane-1-carboxylateythiol and amine/BMPH (N-[β-Maleimidopropionic acid]hydrazide.TFA)/thiol; azide/triarylphosphine; nitrone/cyclooctyne; azide/tetrazine and formylbenzamide/hydrazino-nicotinamide. In certain embodiments, linkers of interest include an aryl linker, such as a p-maleimido aryl linker. For example, each individual polymeric nanowire may be covalently bonded to the bioactive compound through a p-maleimidophenyl linker.

To covalently bond the bioactive compound to the polymeric nanowire, in some embodiments the polymeric nanowire is first prepared (as described above) and covalently conjugated to the bioactive compound, directly or through a linker. In some embodiments, methods include activating one or more of the polymeric nanowire and the bioactive compound by functionalizing with a reactive linker (such as one listed above) and coupling the bioactive compound to the polymeric nanowire by reacting the reactive linkers. In certain embodiments, methods include contacting the composition of individual polymeric nanowires with a composition comprising an aryl isocyanate to produce activated individual polymeric nanowire precursors; and contacting the activated individual polymeric nanowire precursors with a bioactive compound to produce individual polymeric nanowires conjugated to the bioactive compound.

In other embodiments, methods include functionalizing the polymer with a reactive linker and then forming the individual polymeric nanowires as described above. In these embodiments, methods include 1) functionalizing the polymer (e.g., polycaprolactone) with a reactive group, such as a maleimidophenyl isocyanate to produce an activated polymer; 2) preparing individual polymeric nanowires from the activated polymer; and 3) reacting the activated individual polymeric nanowires with a bioactive compound (e.g., an activated bioactive compound with a reactive linker or bioactive compound with a labile reactive group such as a thiol group) to produce individual polymeric nanowires covalently bonded to the one or more bioactive compounds.

Compositions of Individualized Free Floating Polymeric Nanowires

Aspects of the present disclosure also include compositions having individual, free-floating polymeric nanowires. As described above, "individual polymeric nanowires" is meant a composition that includes discrete, free-floating polymeric nanowires which are not joined together, such as being attached to a substrate. In other words, the subject polymeric nanowires are individualized structures and are not connected to each other or bonded to a common substrate. The individual polymeric nanowires have no permanent (e.g., covalent bond) between each other or a bond between the polymeric nanowires and a substrate.

Individual polymeric nanowires according to embodiments of the disclosure have aspect ratios of 2 or greater, such as 3 or greater, such as 4 or greater, such as 5 or greater, such as 6 or greater, such as 7 or greater, such as 8 or greater, such as 9 or greater and including 10 or greater.

Of interest are compositions that include individualize, free-floating nanowires having diameters with range from 10 nm to 500 nm, such as from 15 nm to 400 nm, such as from 20 nm to 300 nm, such as from 25 nm to 200 nm and including from 50 nm to 100 nm. For example, the subject compositions may include individualized, free-floating nanowires prepared by the subject methods have a 200 nm diameter. The subject individualized, free-floating nanowires according to embodiments have a length that is 0.01 µm or more, such as 0.05 µm or more, such as 0.1 µm or more, such as 0.5 µm or more, such as 1 µm or more, such as 2 µm or more, such as 3 µm or more, such as 5 µm or more, such as 10 µm or more, such as 15 µm or more, such as 20 µm or more, such as 25 µm or more, such as 30 µm or more, such as 50 µm or more, such as 100 µm or more, such as 150 µm or more, such as 200 µm or more and including 250 µm or more or more. In certain embodiments, the individual, free-floating nanowires have a length of from 10 µm to 20 µm and a diameter of from 10 nm to 500 nm.

The molecular weight of the nanowires may vary, ranging from 5 kDa to 500 kDa, such as from 10 kDa to 400 kDa, such as from 15 kDa to 300 kDa, such as from 20 kDa to 200 kDa, such as from 25 kDa to 150 kDa and including from 50 kDa to 100 kDa.

In some embodiments, the subject polymeric nanowires do not have a lumen. In other words, the polymeric nanowires have an elongated shape but are not hollow and do not include a conduit that traverses the entire longitudinal axis of the nanowire.

The cross-sectional shape of each individualized, free-floating nanowire may vary depending on the cross-sectional shape of the pores of the template structure used to prepare the subject nanowires. In embodiments, the cross-sectional shape of the polymeric nanowires may be a circle, a semicircle, oval, moon-shaped, crescent shaped, polygonal or other shape or a combination thereof. In some embodiments the cross-sectional shape of the polymeric nanowires is a circle. In other embodiments, the cross-sectional shape of the polymeric nanowires is polygonal, e.g., square, rectangle, pentagon, hexagon, octagon or some other polygon. In still other embodiments, the cross-sectional shape of the polymeric nanowires is oval.

The physicochemical and mechanical properties of the individualized, free-floating polymeric nanowires will vary depending on the type of polymer, size and shape. In certain instances, the subject nanowires absorb solvent (e.g. water) and undergo swelling under physiological conditions (e.g., in contact with blood or plasma), where in certain embodiments, the swelling ratio of the subject nanowires range from 1 to 30, such as from 4 to 27, such as from 5 to 25, such as from 6 to 20, such as from 7 to 18, such as from 8 to 17, such as from 9 to 16 and including a swelling ratio ranging from 1 to 5. Likewise, the polymeric nanowires may have a compressive modulus that ranges from 1 MPa to 35 MPa, such as from 2 MPa to 33 MPa, such as from 3 MPa to 30 MPa, such as from 4 MPa to 28 MPa, such as form 5 MPa to 25 MPa, such as from 6 MPa to 22 MPa, such as from 7 MPa to 20 MPa and including a compressive modulus ranging from 10 MPa to 20 MPa.

Methods for Administering Compositions of Individual Polymeric Nanowires

Aspects of the present disclosure also include methods for administering the subject compositions to a subject. In practicing the subject methods according to certain embodiments, a composition of a plurality of individual polymeric nanowires having a bioactive compound is administered to a subject. By "subject" is meant the person or organism receiving the blood coagulation enhancement. As such, subjects of the invention may include but are not limited to humans and other primates, such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. In certain embodiments, the subject is a human.

In embodiments, the subject compositions of individual polymeric nanowires having one or more bioactive compounds may be administered to a tissue of a subject, including but not limited to integumentary tissue (e.g. sections of the skin), oral tissue (e.g., buccal, tongue, palatal, gums), respiratory tissue (e.g., pharynx, larynx, trachea, bronchi, lungs, diaphragm) gastrointestinal tissue (e.g., esophagus, stomach, liver, gallbladder, pancreas, intestines, colon, rectum and anus.), cardiovascular tissue (e.g., heart, blood vessels), endocrine tissue (e.g., hypothalamus, pituitary gland, pineal body or pineal gland, thyroid, parathyroids, adrenal glands) and genitourinary tissue (kidneys, ureters, bladder, urethra, ovaries, fallopian tubes, uterus, vagina, mammary glands, testes, vas deferens, seminal vesicles, prostate, penis), muscular tissue, nervous tissue (e.g., brain, spinal cord, nerves) as well as soft skeletal tissue (cartilage, ligaments, tendons). Compositions of individual polymeric nanowires having one or more bioactive compounds may be administered to tissue that is either healthy or diseased tissue (e.g., cancerous, malignant, necrotic, etc.)

Any convenient mode of administration may be employed. Modes of administration may include, but are not limited to injection (e.g., subcutaneously, intravenously or intramuscularly), oral administration, intravenous infusion, pulmonary application, rectal application, transdermal application, transmucosal application, intrathecal application, pericardial application, intra-arterial application, intracerebral application, intraocular application, intraperitoneal application or local (i.e., direct) application. Depending on the type of condition, physiology of the subject, and composition, administration of individual polymeric nanowires having one or more bioactive compounds may be local or systemic. In certain embodiments, methods include locally administering a composition of individual polymeric nanowires having one more bioactive compounds. The term "local" is used herein in its conventional sense to refer to directly delivering individual polymeric nanowires having one more bioactive compounds to a location which is at or near the targeted site of administration. For example, in certain instances, methods include injecting a composition of individual polymeric nanowires having one more bioactive compounds at a target site subject (e.g., subcutaneously injecting). Local delivery of ibuprofen may be sustained local delivery or incremental local delivery. For example, local delivery may be constant and continuous, such as over the course of 5 minutes or more, such as 10 minutes or more, such as 15 minutes or more, and including 20 minutes or more. In other instances, local delivery may be delivered incrementally such as delivering the individual polymeric nanowires with bioactive compound at discrete times. For example, individual polymeric nanowires with bioactive compound may be locally delivered every 1 minute, such as every 2 minutes, such as every 5 minutes and including every 10 minutes.

In certain embodiments, the individual polymeric nanowires localize at the target location over a predetermined period of time. The term "localizes" is used herein in its conventional sense to refer to concentrating or accumulating administered individual polymeric nanowires within a predetermined area of the target site, such as within an area of 50 $mm^2$ or less, such as 40 $mm^2$ or less, such as 30 $mm^2$ or less, such as 25 $mm^2$ or less, such as 20 $mm^2$ or less, such as 15 $mm^2$ or less, such as 10 $mm^2$ or less, such as 9 $mm^2$ or less, such as 8 $mm^2$ or less, such as 7 $mm^2$ or less, such as 6 $mm^2$ or less, such as 5 $mm^2$ or less, such as 4 $mm^2$ or less, such as 3 $mm^2$ or less, such as 2 $mm^2$ or less, such as 1 $mm^2$ or less, such as 0.5 $mm^2$ or less, such as 0.1 $mm^2$ or less, such as 0.05 $mm^2$ or less and including a predetermined area of 0.001 $mm^2$ or less. In some instances, 10% or more of the administered individual polymeric nanowires in the composition localizes within an area of the target site, such as 25% or more, such as 50% or more, such as 55% or more, such as 60% or more, such as 65% or more, such as 70% or more, such as such as 75% or more, such as 80% or more, such as 85% or more, such as 90% or more, such as 95% or more, such as 96% or more, such as 97% or more, such as 98% or more, such as 99% or more and including 99.9% or more of the administered individual polymeric nanowires in the composition localizes within an area of the target site, such as within an area of 50 $mm^2$ or less, such as 40 $mm^2$ or less, such as 30 $mm^2$ or less, such as 25 $mm^2$ or less, such as 20 $mm^2$ or less, such as 15 $mm^2$ or less, such as 10 $mm^2$ or less, such as 9 $mm^2$ or less, such as 8 $mm^2$ or less, such as 7 $mm^2$ or less, such as 6 $mm^2$ or less, such as 5 $mm^2$ or less, such as 4 $mm^2$ or less, such as 3 $mm^2$ or less, such as 2 $mm^2$ or less, such as 1 $mm^2$ or less, such as 0.5 $mm^2$ or less, such as 0.1 $mm^2$ or less, such as 0.05 $mm^2$ or less and including a predetermined area of 0.001 $mm^2$ or less.

The dosage of bioactive compound delivered using the subject compositions of individual polymeric nanowires having one or more bioactive compounds may vary, ranging from about 0.01 mg/kg to 500 mg/kg per day, such as from 0.01 mg/kg to 400 mg/kg per day, such as 0.01 mg/kg to 200 mg/kg per day, such as 0.1 mg/kg to 100 mg/kg per day, such as 0.01 mg/kg to 10 mg/kg per day, such as 0.01 mg/kg to 2 mg/kg per day, including 0.02 mg/kg to 2 mg/kg per day. In other embodiments, the dosage may range from 0.01 to 100 mg/kg four times per day (QID), such as 0.01 to 50 mg/kg QID, such as 0.01 mg/kg to 10 mg/kg QID, such as 0.01 mg/kg to 2 mg/kg QID, such as 0.01 to 0.2 mg/kg QID, depending on the dosage protocol as desired. In other embodiments, the dosage may range from 0.01 mg/kg to 50 mg/kg three times per day (TID), such as 0.01 mg/kg to 10 mg/kg TID, such as 0.01 mg/kg to 2 mg/kg TID, and including as 0.01 mg/kg to 0.2 mg/kg TID. In yet other embodiments, the dosage may range from 0.01 mg/kg to 100 mg/kg two times per day (BID), such as 0.01 mg/kg to 10 mg/kg BID, such as 0.01 mg/kg to 2 mg/kg BID, including 0.01 mg/kg to 0.2 mg/kg BID.

In practicing embodiments of the present disclosure, one or more therapeutically effective cycles of treatment may be administered to a subject. By "therapeutically effective cycle of treatment" is meant a cycle of treatment that when administered, brings about the desired therapeutic response with respect to treatment. In these embodiments, treatment regimens may include multiple dosage intervals. A dosage interval is a single administration of the subject compositions. By "multiple dosage intervals" is meant more than one dose of the subject compositions is administered to the subject in a sequential manner. In practicing methods of the invention, treatment regimens may include two or more dosing intervals, such as three or more dosing intervals, such as four or more dosing intervals, such as five or more dosing intervals, including ten or more dosing intervals. The duration between dosage intervals in a multiple dosage interval treatment regimen may vary, depending on the physiology of the subject or by the treatment regimen as determined by a health care professional. In certain instances, the duration between dosage intervals in a multiple dosage treatment regimen may be predetermined and follow at regular intervals. As such, the time between dosing intervals may vary and may be 0.5 hours or longer, such as 1 hour or longer, such as 2 hours or longer, such as 4 hours or longer, such as 8 hours or longer, such as 12 hours or longer, such as 16 hours or longer, such as 24 hours or longer, such as 48 hours or longer and including 72 hours or longer.

Kits

Also provided are kits, where kits at least include one or more, e.g., a plurality of, the components need to prepare a composition of individualized, free-floating polymeric nanowires according to the subject methods. In certain embodiments, the subject kits have one or more of the substrate, polymer composition, template structure as well as reagents for removing the formed polymeric nanowires from the template structure and to purify and wash the formed polymeric nanowires. In embodiments, one or more of each component may be provided as a packaged kit, such as in individual containers (e.g., pouches). Kits may further include other components for practicing the subject methods, such as measuring and application devices (e.g., syringes) as well as containers for solutions such as beakers and volumetric flasks.

In addition, kits may also include step-by-step instructions for how to practice the subject methods, where the instructions may include information about to how apply the polymer composition to the substrate surface, how to remove solvent from the polymer-coated substrate, how to heat the polymer-coated substrate to form a molten polymer surface, how to position the template structure on the heated polymer-coated substrate surface, how to remove the formed polymeric nanowires from the template structure as well as how to purify the formed individualized, free-floating polymeric nanowires. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the protocol for obtaining the instructions may be recorded on a suitable substrate.

EXPERIMENTAL

Example 1—Fabrication of Individualized, Free-Floating Polymeric Nanowires 45 kDa PCL (Sigma Aldrich) is dissolved overnight at 12.5% w/v in trifluoroethanol at 37° C. on a shaker. For in vitro visualization, Nile Red or similar lipophilic dye is dissolved in the polymer solution at this stage. Glass wafers are used as casting substrates after thorough washing with micro-90 surfactant at 2% in distilled water and isopropyl alcohol, and dried with nitrogen then baked on a 120° C. hot plate for 5 minutes. Wafers are allowed to cool before casting is performed.

2 mL of polymer solution is placed in the center of the wafer once on 2" spin coater chuck, and spun at 300 RPM for 10 seconds followed by 1000 RPM for 30 seconds. Wafers are then baked at 110° C. for 2 minutes and set to cool. Aluminum oxide nanoporous membranes are placed onto the polymeric film, and heated to 100° C. for 3 h. The wafers and membranes are allowed to cool and set overnight.

Figure 2A:
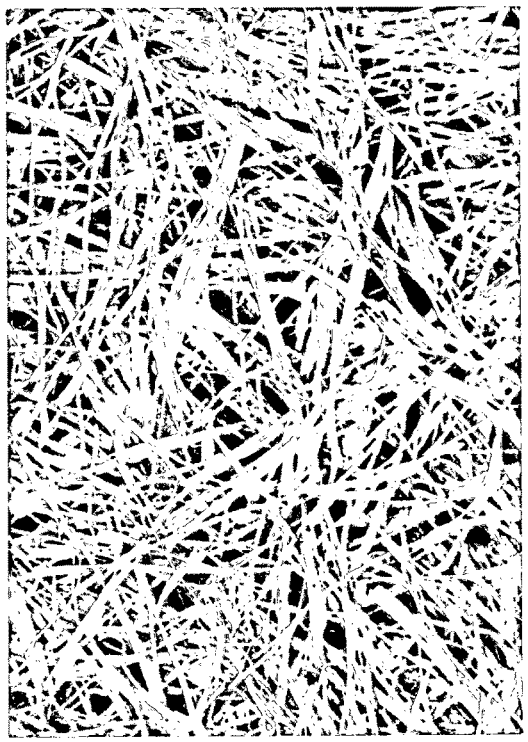
FIGS. 2A and 2B depict scanning electron images of individual, free-floating polymeric nanowires according to certain embodiments of the present disclosure.
Figure 2B:

The membranes are then removed from the surface of the wafers with a razor blade and placed into a 50 mL conical tube. They are then etched in 5M NaOH for 15 minutes on a shaker and 30 minutes in a sonicator at 4° C. PCL nanowires are partitioned via light centrifugation at 200 RPM, removed, diluted 5×and washed 3×at 3000 RPM. They are then filtered through a 40 µm mesh to remove large particulate and the filtrate is washed 2×more. Finished nanowires are tested for pH and stored in 1% Mowiol 5-88 in distilled water to ensure shelf life. Scanning electron images of the nanowires are depicted in FIGS. 2A and 2B.

Example 2—In Vitro Testing of Discrete Polycaprolactone Nanowires with NIH 3T3 Fibroblasts Purified polycaprolactone nanowires were incubated over 24 hours in vitro with NIH 3T3 fibroblast cells. Nanowires that had previously been incorporated with Nile Red were taken from a stock dispersion at 1:10 and 1:100 dilutions corresponding to high and low doses respectively. These wires were dispersed in cell culture medium (10% fetal bovine serum in DMEM) in a cold sonicator for 20 minutes before being placed into a cell culture well.

Staining and imagine: NIH 3T3 cells were concurrently placed into the wells at varying densities of 1000-100,000 cells/mL of cell culture medium and cultured with the nanowires in the wells for 24-72 h. Cells were then fixed with paraformaldahyde/acetone/methanol and permeabilized with surfactants such as triton X-100 to allow for staining. Cells in slide 9 were stained with phalloidin (green) and DAPI (blue) to image the actin cytoskeleton and cell nuclei, respectively. Nanowires are shown in the red channel via the Nile Red dye contained inside them. Cells were then imaged using a 6D Nikon epifluorescence microscope for cell morphology and phenotypic changes as a result of nanowire application. Nanowires appear to downregulate the myofibroblast phenotype as evidenced by a rounder cell morphology and more diffuse actin cytoskeleton.

Cyauant Assay: This is proliferation assay counts the amount of DNA present in each well, which is compared to a known standard number of the relevant cell type or an absolute amount of control DNA. Cells were thrice washed in PBS, removed from the surface of the wells via trypsin, concentrated then frozen at −80 C overnight in 100,000-1,000,000 cells per mL. Cells are then thawed and resuspended in cell lysis buffer and CYQUANT dye for 5 minutes at room temperature, plated in a dilution series and read on a fluorescence plate reader. Nanowires do not appear to have a significantly deleterious effect on the proliferation of the NIH 3T3 cells tested in this assay.

TUNEL: This assay measures the fragmented DNA of apoptotic cells by catalytically incorporating fluorescein-12-dUTP at 3'-OH DNA ends using the Terminal Deoxynucleotidyl Transferase enzyme (rTdT), which forms a polymeric tail. The fluorescein-12-dUTP-labeled DNA then can be visualized directly by fluorescence microscopy. Cells are fixed and permeabilized in the same fashion as above and subsequently incubated with a solution of the TdT enzyme and labeled 12-dUTP, and cells are counted visually or with image processing software to asses the percent positive for incorporation, which indicates a cell about to undego apoptosis. Literature accepted values of ~6-7% are considered normal for NIH 3T3 cells and the nanowires do not appear to cause additional apoptosis compared to cell culture media alone, whereas spherical nanoparticles of the same diameter as the nanowires do.

Figure 3A:
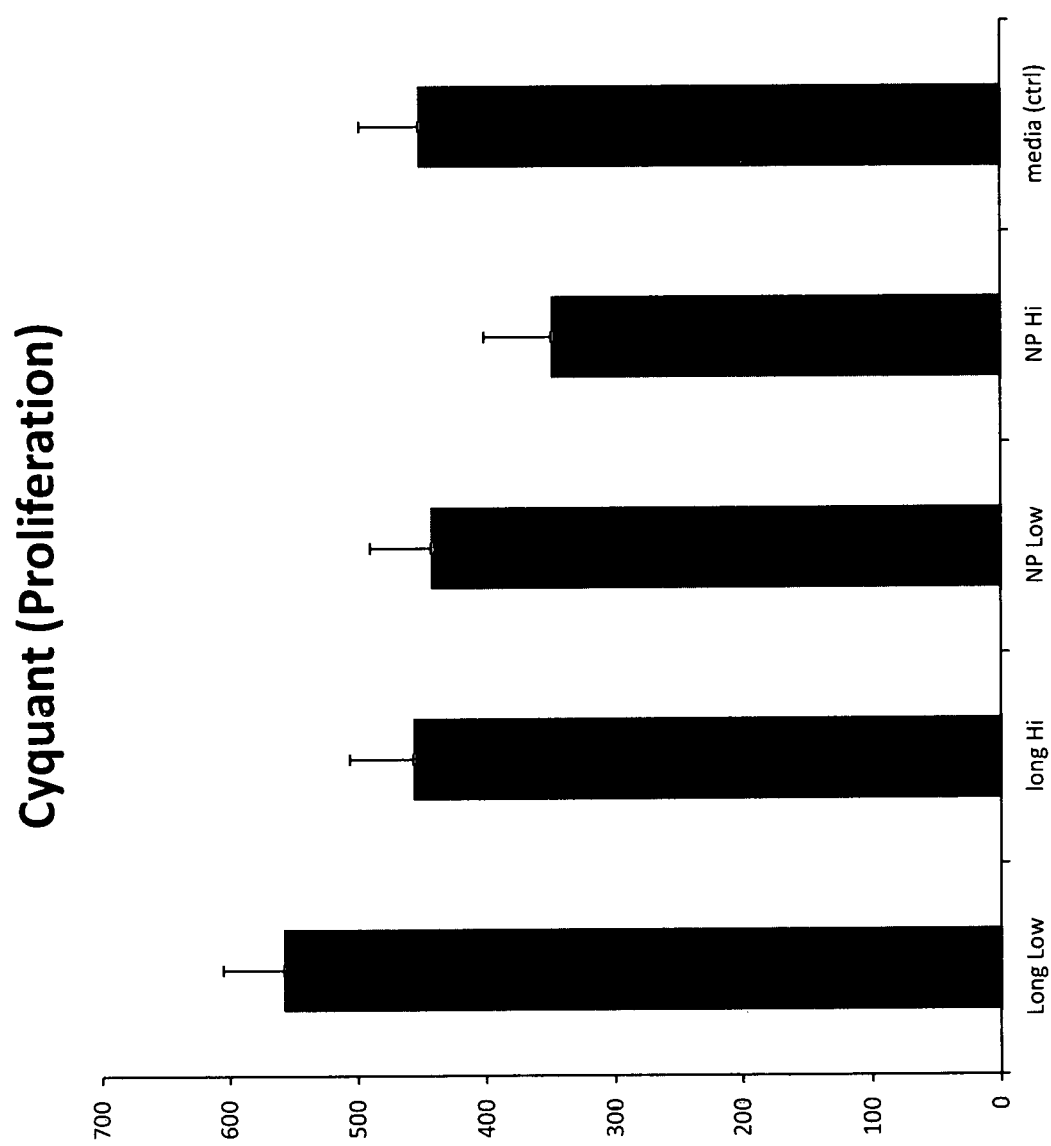
FIG. 3A depicts results from a Cyquant Assay of NIH 3T3 fibroblast cells incubated with a composition of individual, free-floating polymeric nanowires according to certain embodiments of the present disclosure.
Figure 3B:
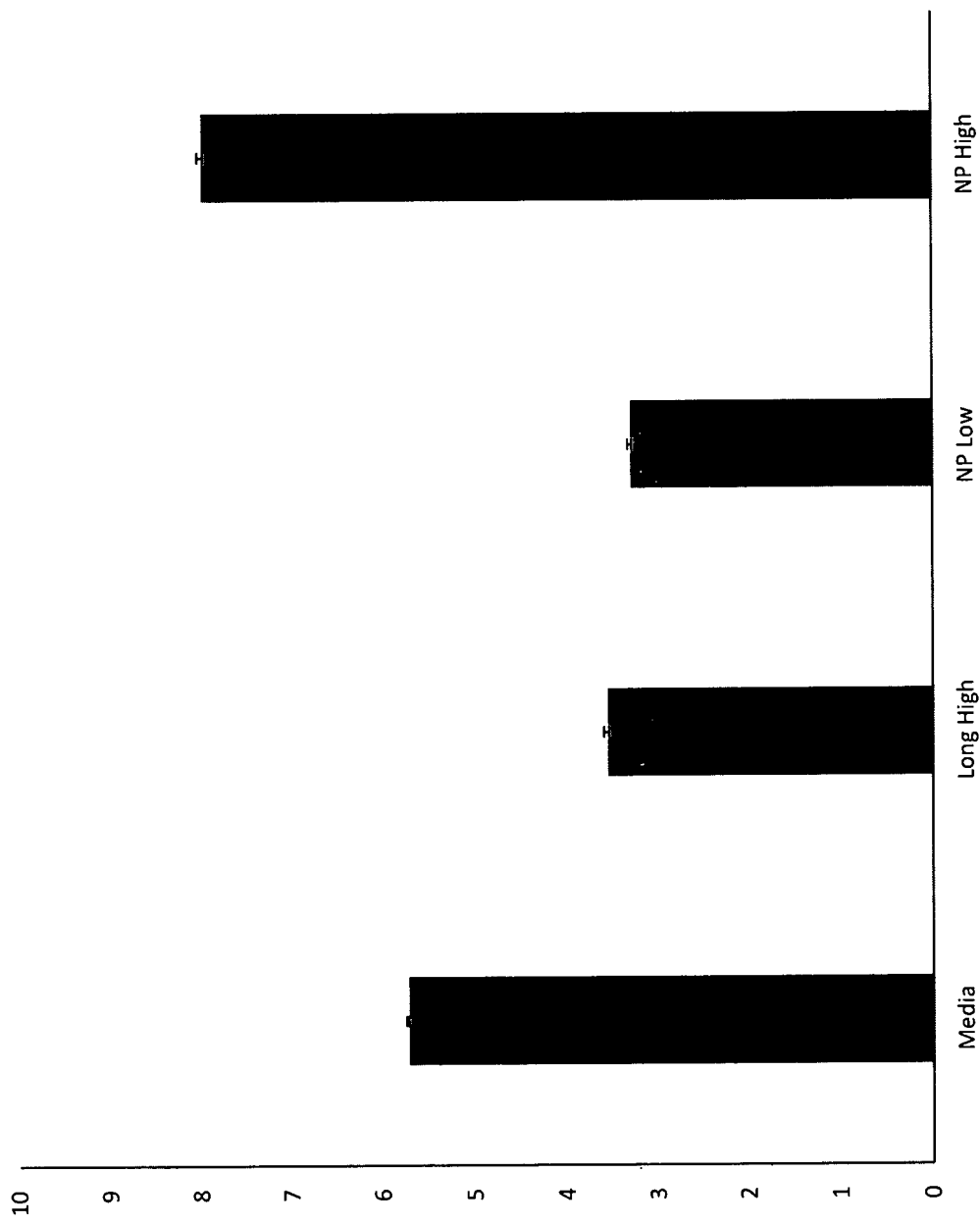
FIG. 3B depicts results from a TUNEL assay of NIH 3T3 fibroblast cells incubated with a composition of individual, free-floating polymeric nanowires according to certain embodiments of the present disclosure.

The nanowires showed no negative effects on cell survival. This was assessed by in vitro by viability, proliferation and apoptosis assays with high and low concentration of polycaprolactone nanowires. FIG. 3A depicts results of Cyquant Assay that proliferation of the fibroblast cells was unaffected by the nanowires. Apoptosis was evaluated by TUNEL assay (FIG. 3B). These assays demonstrate that the presence of the nanowires had no effect on the proliferation and apoptosis of the cells.

Example 3—Cell Morphology and Actin Cytoskeleton in the Presence of Polymeric Nanowires Purified polycaprolactone nanowires were incubated with cells in vitro to determine their effect on cellular morphology. Wires were incubated with cells for 24-48 h concurrently with nanowires previously dispersed in sterile cell culture media. After the time course had finished, cells were washed thrice with fresh PBS, fixed with 4% paraformaldehyde, permeabilized with a suitable surfactant such as 1% triton x-100 and imaged via fluorescent microscope to observe phenotypic and morphological changes of cells grown in contact with PCL nanowires.

Figure 4:
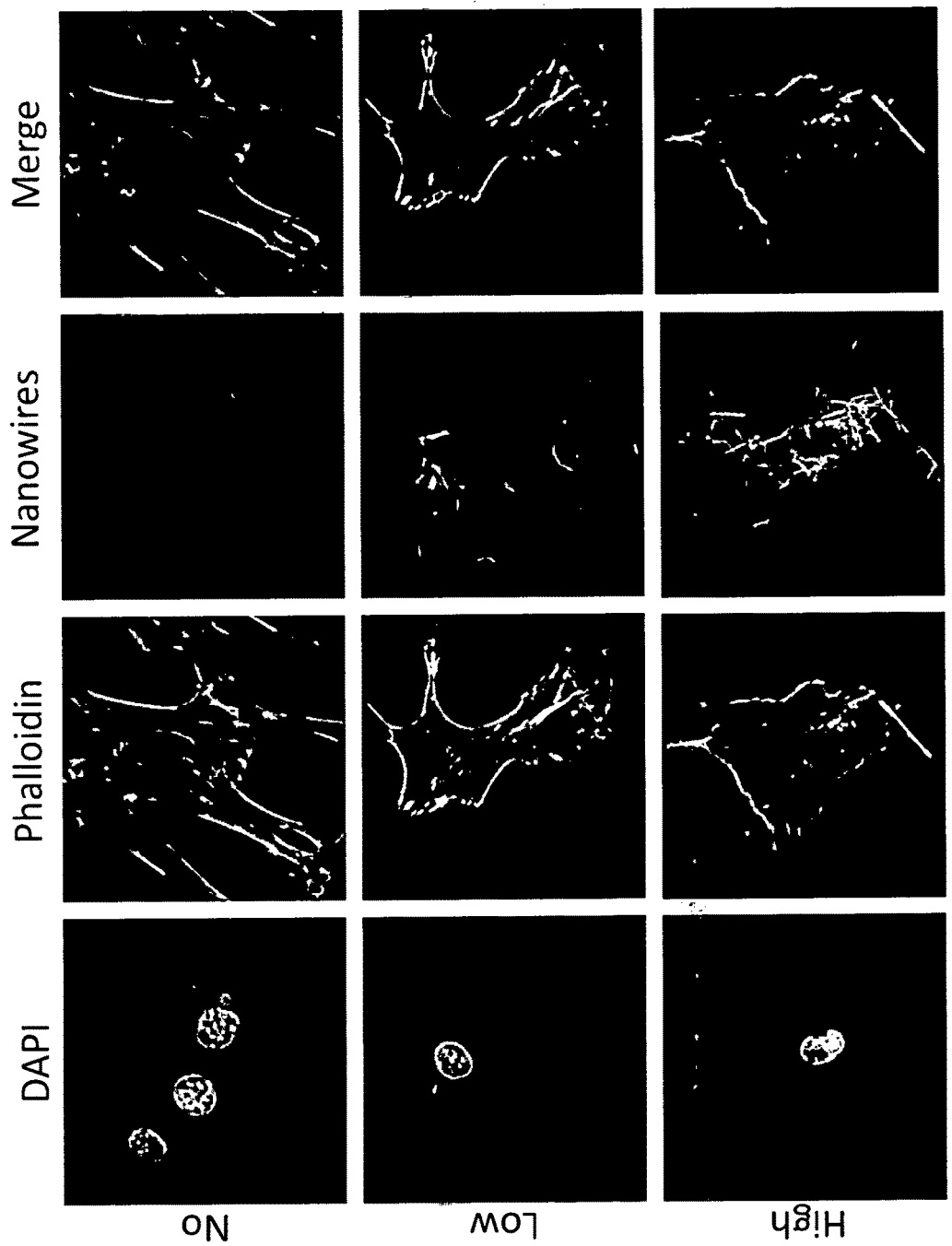
FIG. 4 depicts the change is cellular morphology and actin cytoskeleton of the cells in the presence and absence of the nanowires.

FIG. 4 depicts the change is cellular morphology and actin cytoskeleton of the cells in the presence and absence of the nanowires.

Example 4—Effect of Nanowires on TGF-β and Collagen Expression

Purified polycaprolactone nanowires were incubated with cells in vitro to determine their effect on TGF-β and Collagen Expression. Experimental protocol was the same as Example 3, except the cells were grown in 96 well plates with suitably reduced volume and numbers of nanowires. Cells were then lysed with appropriate lysis buffer and mRNA was extracted and purified for RTqPCR to assess gene expression of cells in contact with PCL nanowires.

Figure 5:
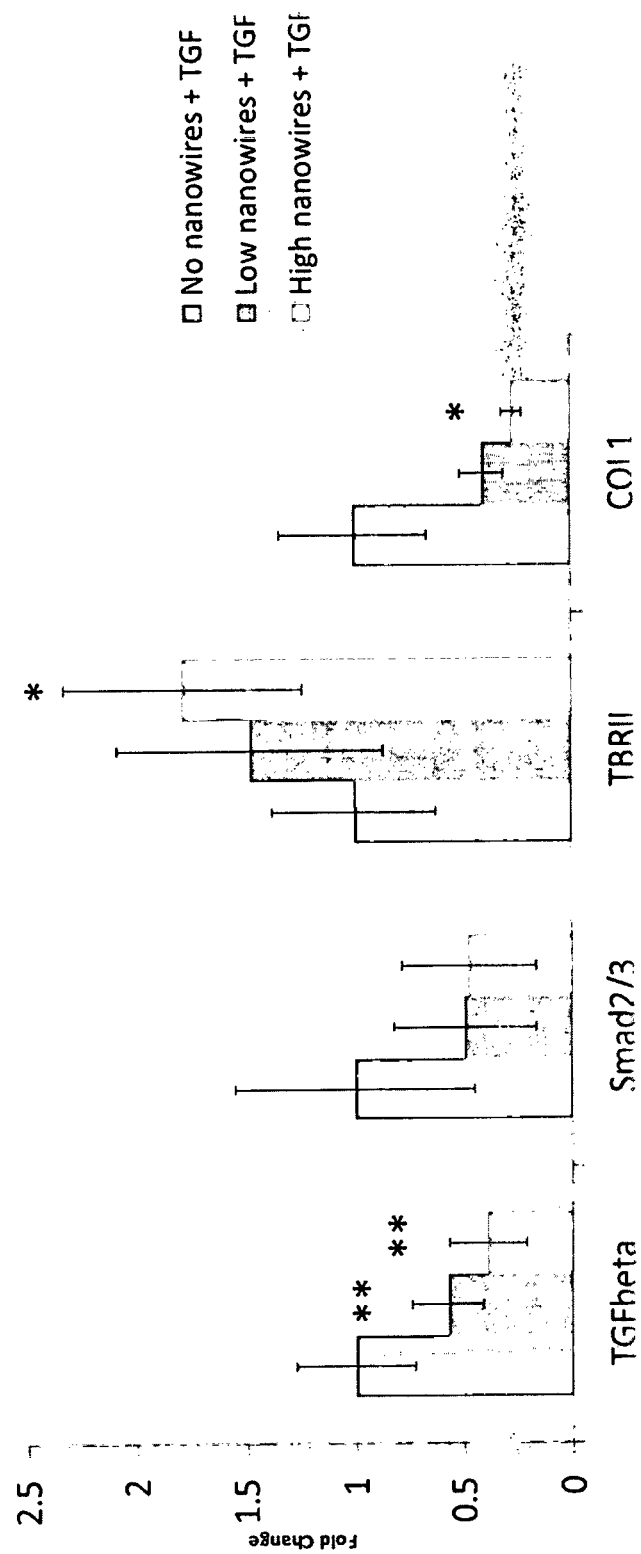
FIG. 5 depicts the change in expression of TGF-β, Smad 2/3, TBRII and COL1 in the presence of a low concentration of purified polycaprolactone nanowires, a high concentration of purified polycaprolactone nanowires and in the absence of the nanowires.

FIG. 5 depicts the change in expression of TGF-β, Smad 2/3, TBRII and COL1 in the presence of a low concentration of purified polycaprolactone nanowires, a high concentration of purified polycaprolactone nanowires and in the absence of the nanowires. These studies demonstrate that the presence of both high and low concentrations of the nanowires decrease TGF-β and collagen expression.

Example 5—In vivo tolerability of Nanowires

Purified polycaprolactone nanowires were injected (10× 50 μL) into shaved mouse dorsal skin of B6 mice (6-8 weeks old, n=3) Sterile saline carrier was used as a control.

Figure 6:
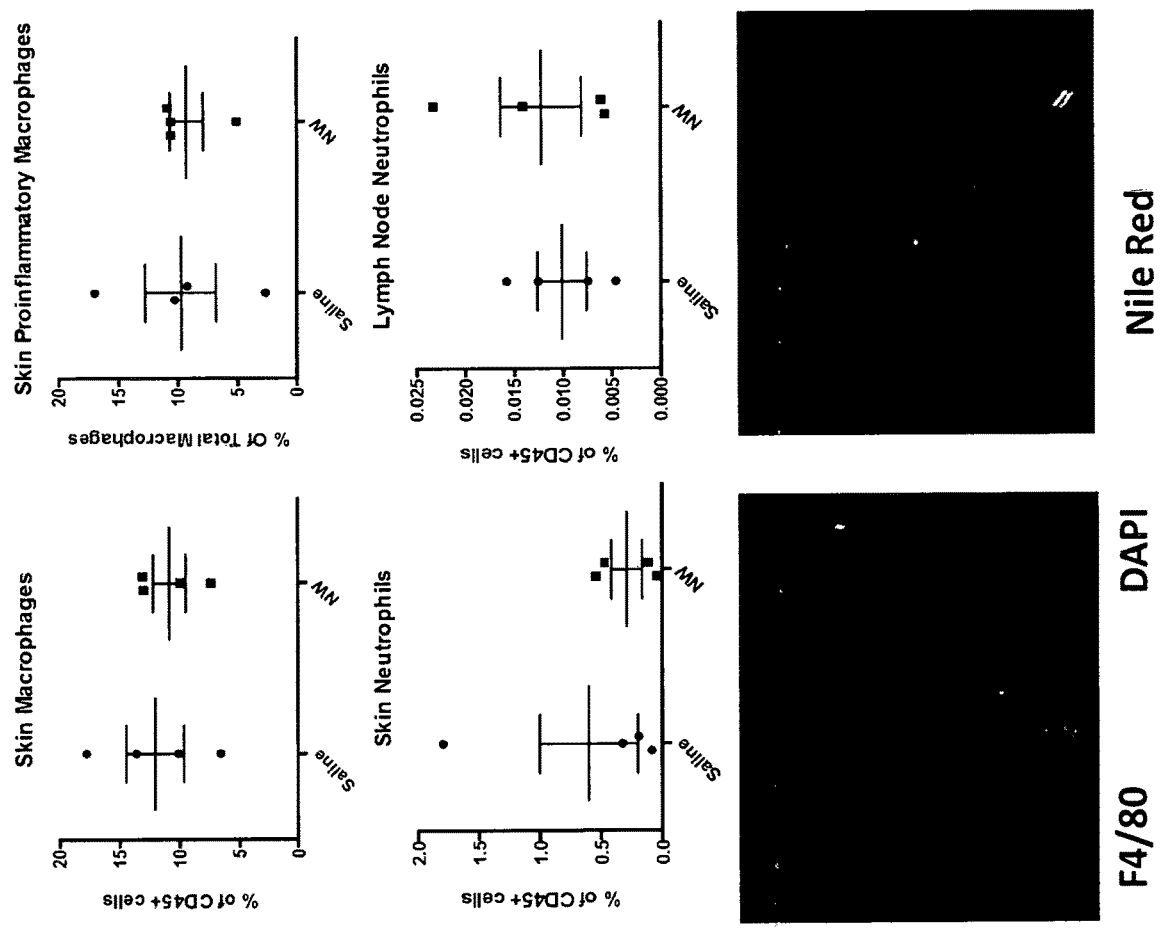
FIG. 6 depicts the effect of the nanowires on skin macrophages, skin neutrophils, skin inflammatory macrophages and lymph node neutrophils.

FIG. 6 depicts the effect of the nanowires on skin macrophages, skin neutrophils, skin inflammatory macrophages and lymph node neutrophils. The results demonstrate that minimal inflammatory effect is observed from both global skin digestion as well as by local IF macrophage staining.

Example 6—Antibody conjugation to Nanowires

Figure 7A:
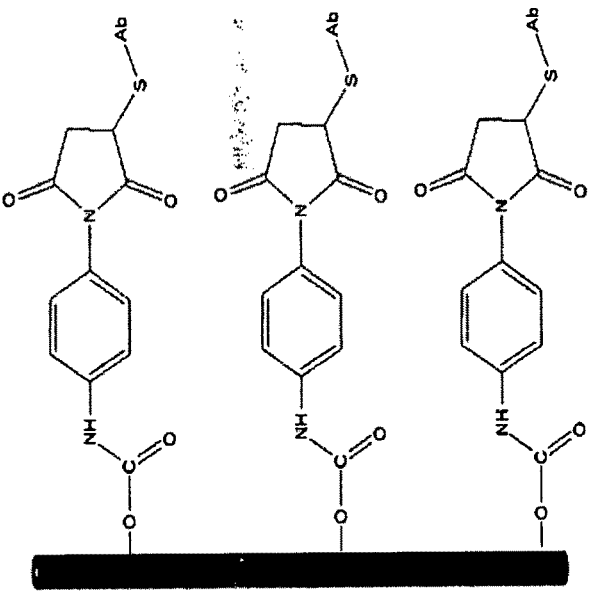
FIG. 7A depicts a scheme for preparing maleimide-functionalized polycaprolactone nanowires according to certain embodiments.
Figure 7A:
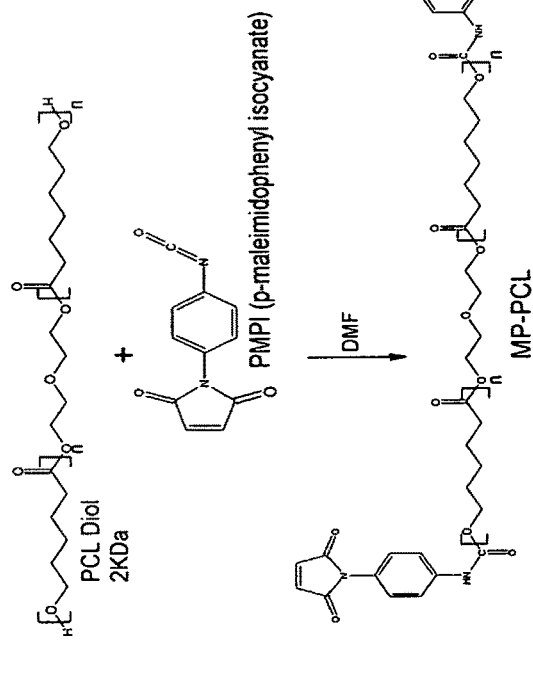
Figure 7B:
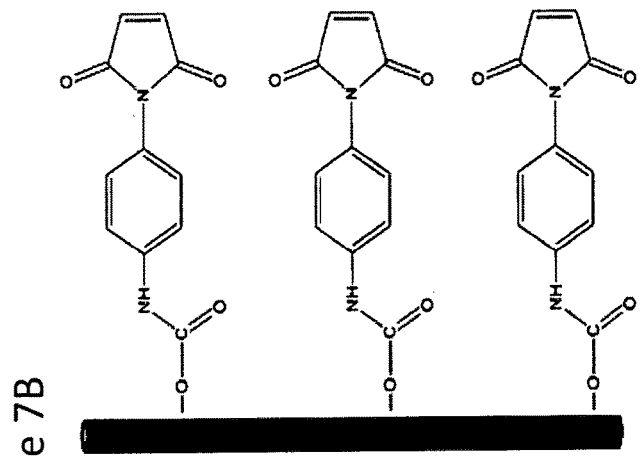
FIG. 7B depicts conjugating the maleimide-functionalized polycaprolactone nanowires to an antibody according to certain embodiments.

Polycarprolactone nanowires were covalently bonded to antibodies through a maleimide end group via a non-cleavable linkage. A maleimide group is conjugated to the PCL polymer with a reactive p-maleimidophenyl isocyanate to produce an activated PCL-maleimide polymer starting material. Discrete, individual PCL nanowires are prepared as described in Example 1 with reactive maleimide on the surface of the nanowires. FIG. 7A depicts, according to certain embodiments of the present disclosure, a scheme for preparing maleimide-functionalized polycaprolactone nanowires and FIG. 7B depicts reacting the activated polycaprolactone nanowires with a thiol group on an antibody to produce an individual polycaprolactone nanowire covalently bonded through a linker to an antibody.

Experimental Designs and Methods 45 kDa polycaprolactone is dissolved overnight at 12.5% w/v in trifluoroethanol at 37° C. on a shaker. For in vitro visualization, Nile Red or similar lipophilic dye is dissolved in the polymer solution at this stage. Glass wafers are used as casting substrates after thorough washing with micro-90 surfactant at 2% in distilled water and isopropyl alcohol, and dried with nitrogen then baked on a 120° C. hot plate for 5 minutes. Wafers are allowed to cool before casting is performed.

2 mL of polymer solution is placed in the center of the wafer once on 2" spin coater chuck, and spun at 300 RPM for 10 seconds followed by 1000 RPM for 30 seconds. Wafers are then baked at 110° C. for 2 minutes and set to cool. Aluminum oxide nanoporous membranes are placed onto the polymeric film, and heated to 100° C. for 3 h. The wafers and membranes are allowed to cool and set overnight.

The membranes are then removed from the surface of the wafers with a razor blade and placed into a 50 mL conical tube. They are then etched in 5M NaOH for 15 minutes on a shaker and 30 minutes in a sonicator at 4° C. PCL nanowires are partitioned via light centrifugation at 200 RPM, removed, diluted 5× and washed 3× at 3000 RPM. They are then filtered through a 40 μm mesh to remove large particulate and the filtrate is washed 2× more. Finished nanowires are tested for pH and stored in 1% Mowiol 5-88 in distilled water to ensure shelf life.

Synthesis of Maleimide-Functionalized Polycaprolactone (PCL-MAL)

Figure 8:
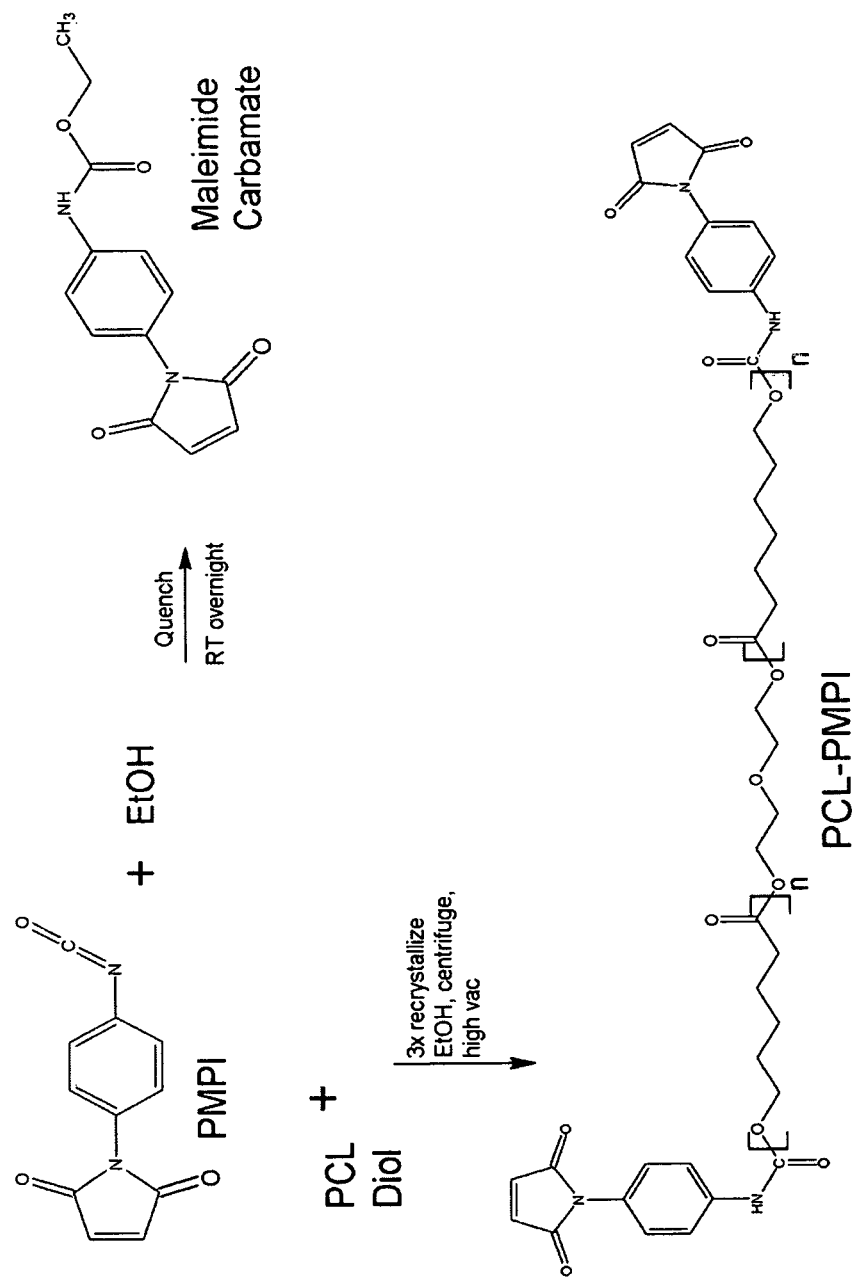
FIG. 8 is a reaction scheme for preparing p-maleimidophenyl-functionalized polycaprolactone according to certain embodiments.

FIG. 8 depicts a reaction scheme for preparing p-maleimidophenyl-functionalized polycaprolactone according to certain embodiments of the present disclosure. p-maleimidophenyl isocyanate (PMPI) was dissolved in rigorously dried DMF as a cosolvent and added to the PCL-PMPI at a 2.5 molar excess. Flask was kept under argon overnight and stirred at 40 C during reaction progress. Excess PMPI was quenched with dry ethanol overnight to form a phenylmaleimide carbamate. The product is then washed 3× on ice in dry ethanol to remove carbamate and centrifuged to pellet product. Final mass yield was ~75% and analyzed by mass spec and NMR to verify conjugation and amount of starting material remaining.

Conjugation of PCL Nanowires to Antibody

Solvent-polymer mixture for conjugable nanowires now consists of 30% by weight of the PCL-Mal product. This is then cast and fabricated exactly as stated above.

For conjugation to antibody, first thaw IGg species from −80° C. freezer and allow to reach room temperature. Dilute to approximately 2× the desired final concentration when with nanowires in reduction buffer. Final concentration should be 0.1-1 mg/ml of antibody species, which is roughly 1000× excess. Make a fresh stock solution of TCEP (tris(2-carboxyethyl)phosphine) in reduction buffer (D-PBS containing 0.04% EDTA) at 1 mg/mL. Add 4.5 molar excess of TCEP to 2× antibody stock to reduce on average 2 disulfide bonds. TCEP will selectively reduce in the hinge region of the antibody and not interfere with the antigen binding region, and is an orthogonal reductant—meaning it does not need to be removed before addition of the nanowires (no dialysis step required). Place on shaker plate for 1 h at 37° C.

Add to nanowires at a 0.5× dilution from stock (5 anapore wafers to 1 mL of solution is considered a 1× dispersion). Place nanowire-antibody solution in foil and on shaker plate at room temperature for 2 h. Product is stored at 4° C. until use.

Conjugation of PCL Nanowires to Labelled Antibody

Fluorescently labeled (AlexaFluor 488) antibody (IgG) was conjugated to polycaprolactone nanowires. AlexaFluor488-IgG was covalently bonded to polycaprolactone as described below:

Materials 45 kDa Polycaprolactone, TFE, anapore membranes (20 nm), PCL-PMPI reagent (2 kDa PCL terminated in phenyl maleimide. Reduction buffer (D-PBS with 0.04% EDTA).

Methods

The highest weight % of 2 kDa PCL-PMPI possible while maintaining the film's ability to be handled and templated is 30%. Dissolve this 30% PCL-PMPI+70% 45 kDa PCL in trifluoroethanol at 125 total mg/ml.

Templated nanowires were etched in room temperature 5M NaOH on shaker for 20 minutes or until >90% visible anapore template is completely removed. Ratio of 3 wafers to 50 mL (large conical) of etching solution was used. Sonicate on ice for 20 minutes. Bottom 10 mL of solution in conical (which contains leftover alumina that settles during sonication, polymer should float) was discarded. Top ~30 mL was taken and diluted 1/3 in ice cold DI water to slow degradation and centrifuge at 5° C., 2500 rpm for 8-10 minutes. Nanowires partition to middle of conical or pellet at the bottom.

Etchant was removed and samples combined in ice cold DI water, wash 2× more. ~1 mL of cold 1% PVA was added to 10 mL of nanowire suspension, sonicated briefly, strained through filter mesh using squeeze bottle to help push through mesh.

Wash 2× more in ice cold DI water, monitor pH with paper. Finish with an additional final wash in reduction buffer. Spin down, remove supernatant (the buffer), and resuspend in fresh reduction buffer to 5 mL. This will ensure no aluminum is present in the final product which will interfere with conjugation.

1. First thaw IGg species from −80° C. freezer and allow to reach room temperature.
2. Dilute to approximately 2× the desired final concentration when with nanowires in reduction buffer. Final concentration should be 0.1-1 mg/ml of antibody species, which is roughly 1000× excess. If antibody is valuable the excess can be reduced.
3. Make a fresh stock solution of TCEP (tris(2-carboxyethyl)phosphine) in reduction buffer at 1 mg/mL.
4. Add 4.5 molar excess to 2× antibody stock to reduce on average 2 disulfide bonds. TCEP will selectively reduce in the hinge region of the antibody and not interfere with the antigen binding region, and is an orthogonal reductant—meaning it does not need to be removed before addition of the nanowires (no dialysis step required).
5. Place on shaker plate for 1 h at 37° C.
6. Add to nanowires at a 0.5× dilution from stock (5 anapore wafers to 1 mL of solution is considered a 1× dispersion).
7. Place nanowire-antibody solution in foil and on shaker plate at room temperature for 2 h.
8. Store at 4° C. until use.

Before use, wash 3× in D-PBS to remove free antibody and resuspend in sterile saline for in vivo use or appropriate buffer for ELISA or other assay as required.

Figure 9B:
FIG. 9B depicts non-reduced ABO95 IgG antibodies labelled with AlexaFluor488 covalently bonded to polycaprolactone nanowires.
Figure 9A:
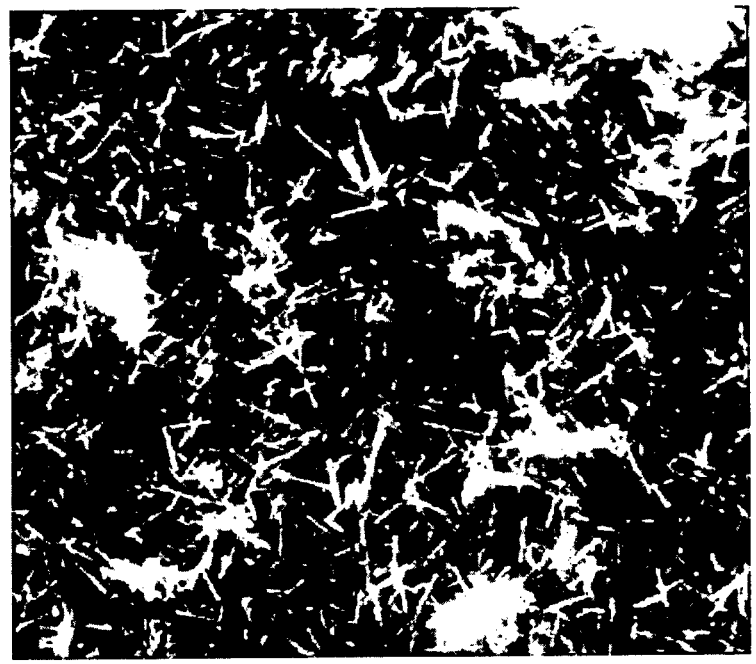
FIG. 9A depicts reduced AB095 IgG antibodies labelled with AlexaFluor488 covalently bonded to polycaprolactone nanowires.

This experiment demonstrates binding of a biological species to the surface of the nanowires without sacrificing wire stability in solution or their structural integrity. FIGS. 9A-9B depict fluorescently labelled antibody conjugated to individual polycaprolactone nanowires according to these embodiments. FIG. 9A depicts reduced AB095 IgG antibodies labelled with AlexaFluor488 covalently bonded to polycaprolactone nanowires. FIG. 9B depicts non-reduced AB095 IgG antibodies labelled with AlexaFluor488 covalently bonded to polycaprolactone nanowires.

Cytokine Inhibitor Antibody Conjugated Nanowires

Figure 10:
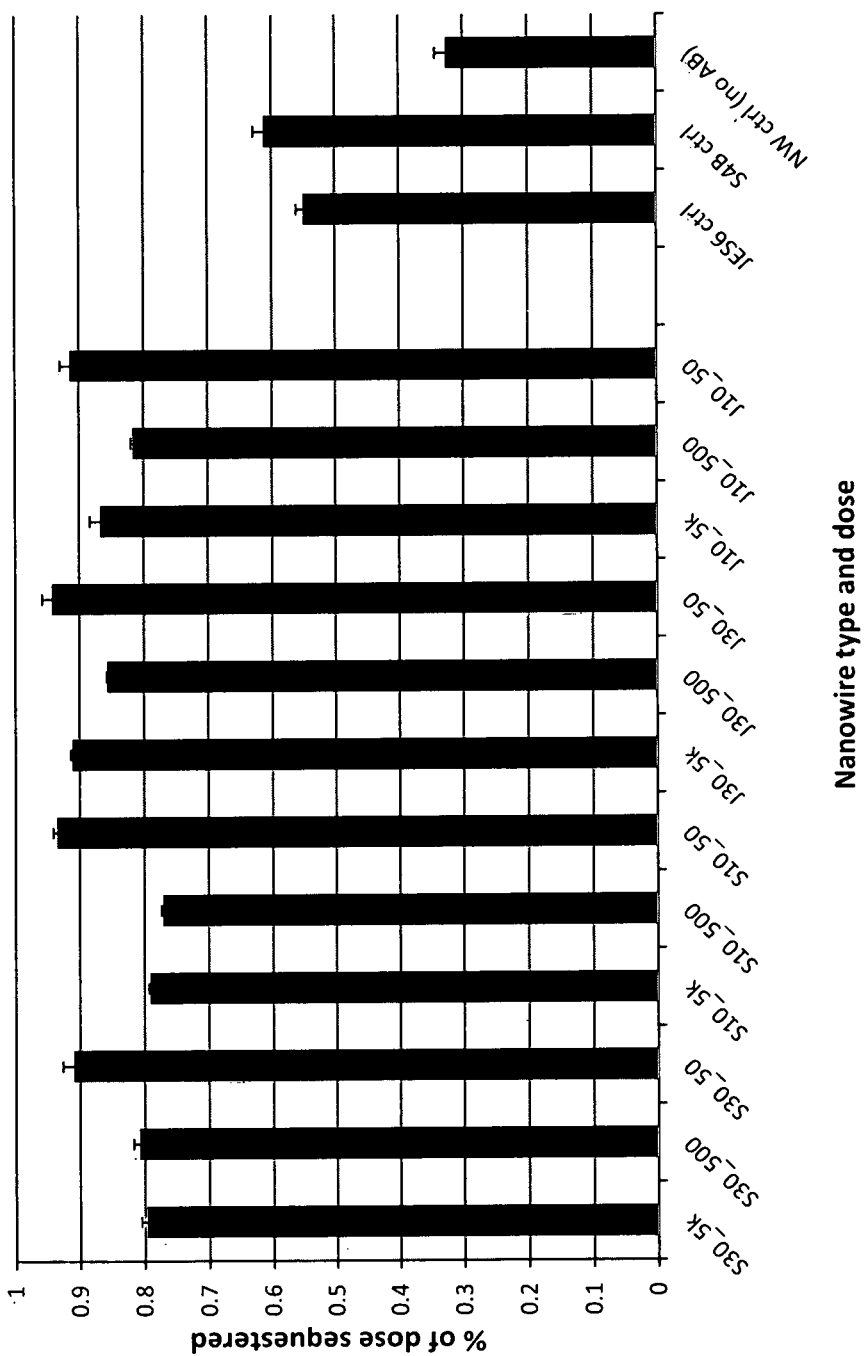
FIG. 10 depicts the percent of dose sequestered by different types of nanowires and dose amounts according to certain embodiments.

Mouse IL-2 binding antibody was conjugated to discrete, free-floating polycaprolactone nanowires. Covalently bound mouse IL-2 binding antibody was prepared similarly as described above for IgG bound polycaprolactone nanowires. Two different clones (S4B6-1 and JES6-1) were tested as test articles and found that both can successfully sequester IL-2 when conjugated to the nanowires at concentration 10× higher than what is found in the subcutaneous tissue. Non-specific binding controls were performed to assess the ability of the nanowires to adsorb to IL-2. FIG. 10 depicts the percent of dose sequestered by different types of nanowires and dose amounts.

Evaluation of Nanowires in Subcutaneous Animal Model of Delivery

A wild type murine in vivo study to assess the nanowire bound antibody's ability to interact with local tissue when injected into the skin was conducted. A three arm study with bare nanowires, Anti-IL-2 nanowires and free antibody were injected 10×50 μL in each mouse back and harvested after 3 days. ELISA was performed to assess the exact dose equivalent of active antibody to introduce into the third group. Dorsal skin and six skin draining lymph nodes were harvested and stained for flow cytometry analysis.

Murine Harvest Protocol

Materials

18 C57BL/6 mice

Digestion cocktail

For 15 mL:

30 mg (2 mg/ml) collagenase XI (4129.2 U/ml, Sigma, # C9407-100 mg, Collagenase digestion activity 1240 U/mg), 7.5 mg (0.5 mg/ml) hyaluronidase (260 U/ml, Sigma, # H3506-100 mg, 451 U/mg)

1.5 mg (0.1 mg/ml, ICN) DNase (0.1 mg/ml, ICN)

Interventions:

Nanoparticles only

Nanoparticles+anti-IL2

S4B6-1 Anti-IL2 only (50 ng)

Experimental Design

| Group | Mice | Treatment | Harvest |
| --- | --- | --- | --- |
| A | 6 female B6 | SQ Nanowires | Day 3 |
| B | 6 female B6 | SQ Nanowires + anti-IL2 | Day 3 |
| C | 6 female B6 | 50 ng anti-IL2 SQ | Day 3 |

Protocol:

Day 0:

Anesthetize mice with isofluorane. Shave mice dorsal skin. Inject 50 μL of nanowires SQ in 10 injection sites on back.

Day 3:

Harvest mice

Mouse Harvest Protocol:

Sacrificed mouse. First remove skin draining lymph nodes (inguinal, axillary, and brachial), then remove skin from mouse. Harvest back skin only, aiming for area dosed with nanowires.

Digestion:

Scrape fat off of skin in petri dish using forceps. Weigh skin.

Skin: place in shallow top of petri dish. Put 0.5 mL aliquot of skin digestion cocktail onto skin to wet it. Mince skin with scissors until there is no resistance. Transfer to 50 mL conical with 3 mL digestion cocktail. When skin samples from all mice have been collected, put in 37 degree bacterial incubator to shake (250 RPM) for 45 minutes.

Lymph nodes: Mash with rubber end of syringe through 100 um filter, and wash filter/syringe with 8 mL C10 medium. Leave on ice until skin is processing. Spin down, resuspend at 10 mL C10 medium and count. Resuspend at 8×10^6 cells/mL.

Once finished processing, put on ice. Add 10 mL C10 and vortex and filter sample through 100 micron filter. Spin down (4 C, 5 min 1500 RPM). Remove supernatant and resuspend in 1 mL C10. Count on nucleocounter. Spin down and resuspend in at 16×10^6 cells/mL. Stain 1-2×10^6 cells with myeloid/T cell panel immediately.

1 million cells for each collective lymph node sample and 2 million cells for each skin sample are stained for flow cytometry. See flow panel for antibody type and stains.

Flow Staining:

1. Prepare surface antibody mix (50 μL excess) in PBS+2% FBS. Wash cells in plate in PBS+2% FBS. Spin down at 2000 RPM 4 C for 2 min.

2. Remove supernatant and resuspend in 100 µL of Ab mix for skin and 50 µL Ab for LN.
3. Incubate at 4 C for 30 minutes.
4. Add 150 µL PBS/FBS and spin down as before. Wash 1× with 200 µL PBS/FBS.
5. Reconstitute Fixation/Permeation solution (1:4) and add 50 µL of Fix/Perm (ebio).
6. Incubate at 4 C for 30 minutes.
7. Add 150 µL Perm wash, spin for 4 min at 4 degC 2000 RPM
8. Prepare Ab mixes in Perm Buffer according to panel (50 µl in excess).
9. Add 100 µl Ab mix to each skin sample and 50 µL for LN.
10. Incubate 30 min at 4° C. in the dark
11. Add 150 µl Perm Buffer to each sample
12. Centrifuge for 4 min at 4° C. and 2000 rpm.
13. Wash 1× with 200 µL Perm buffer, centrifuge as before.
14. Resuspend in 150 µL PBS/FBS.
15. Analyze on Flow Cytometry.

Cryosectioning: Locate nanowire nodule in dorsal skin skin section, trim to approx. 0.5 cm×0.5 cm and place in OCT inside cassette. Freeze in isopentane chilled by liquid nitrogen, then store at −80 C. Sectioning on cryostat at 20 um sections, stored at −20 C until section staining carried out.

Tissue Staining:
Buffers:
1. Formaldehyde: 16%, methanol free, Polysciences, Inc. (cat#18814), use fresh and store opened vials at 4° C. in dark. Dilute 1 in 4 in 1×PBS to make a 4% formaldehyde solution.
2. Blocking Buffer: (1×PBS/5% normal serum/0.3% Triton™ X-100): To prepare 10 ml, add 0.5 ml normal serum from the same species as the secondary antibody (e.g., Normal Goat Serum (#5425) to 9.5 ml 1×PBS) and mix well. While stirring, add 30 µl Triton™ X-100.
3. Antibody Dilution Buffer: (1×PBS/1% BSA/0.3% Triton™ X-100): To prepare 10 ml, add 30 µl Triton™ X-100 to 10 ml 1×PBS. Mix well then add 0.1 g BSA (#9998), mix.

Block specimen in blocking buffer for 60 min.
1. While blocking, prepare primary antibody by diluting as indicated on datasheet in antibody dilution buffer.
2. Aspirate blocking solution, apply diluted primary antibody.
3. Incubate overnight at 4° C.
4. Rinse three times in 1×PBS for 5 min each.

NOTE: If using a fluorochrome-conjugated primary antibody, then skip to Step 7.
5. Incubate specimen in fluorochrome-conjugated secondary antibody diluted in antibody dilution buffer for 1-2 hr at room temperature in the dark.
6. Rinse three times in 1×PBS for 5 min each.
7. Coverslip slides with Prolong® Gold Antifade Reagent (#9071) or Prolong® Gold Antifade Reagent with DAPI (#8961).
8. For best results, allow mountant to cure overnight at room temperature. For long-term storage, store slides flat at 4° C. protected from light.

A blank nanowire experiment was run to a significant inflammatory infiltrate was generated. Injections formed nanowire 'depots' near sites of injection between subcutaneous fat and skin, and were not washed away within 5 days of injection. Frozen sections were fixed and stained with F4/80 to visualize macrophage infiltrate, and skin was harvested and stained with a myeloid panel to assess neutrophil and macrophage population changes versus saline control (FIG. 6). No difference was observed both locally and with wholesale dorsal skin digestions, which suggests the individual polycaprolactone nanowires are well tolerated in the tissue. FIG. 6 depicts flow cytometry analysis of myeloid cells in dorsal skin of BLK/6 mice injected with PCL nanowires. FIG. 6 depicts Nile Red stained nanowires injected in myeloid cells in dorsal skin of BLK/6 mice and stained for macrophage infiltrate. Analysis was done at 5 days post injection.

Figure 11:
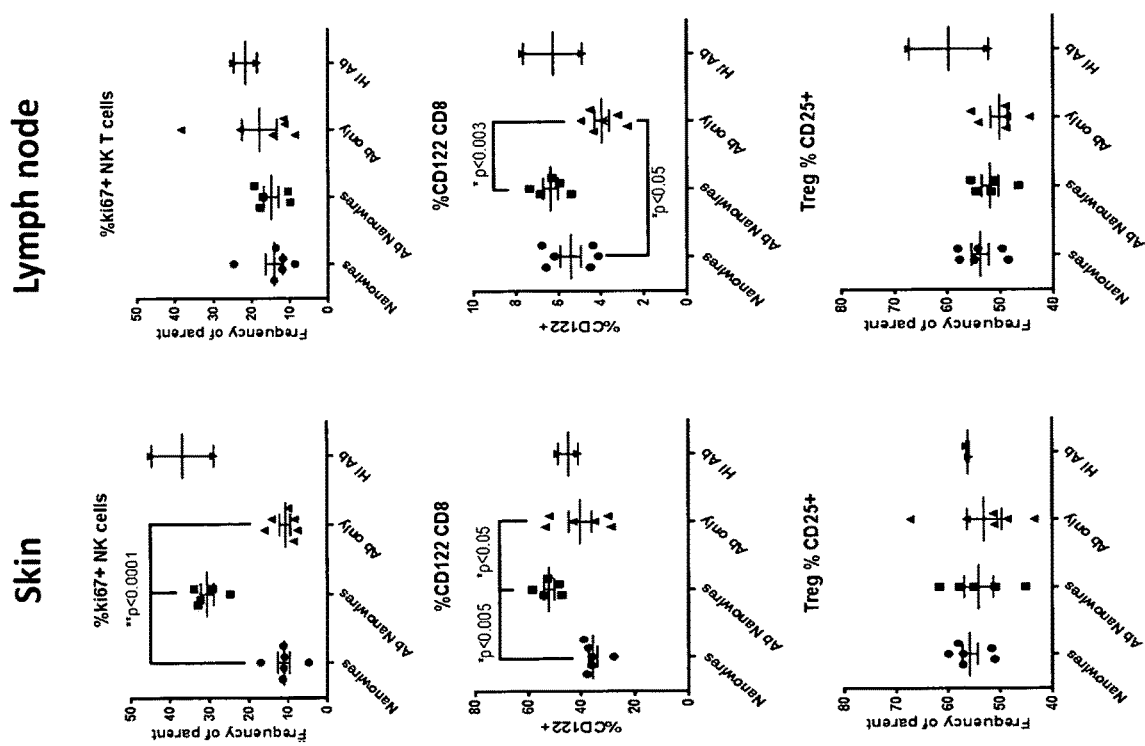
FIG. 11 depicts flow cytometry analysis of T-cell populations according to certain embodiments.

Nanowires covalently bonded to IL-2 binding antibody using blank nanowires as a control were injected. (no difference was seen in T-cell population between blank wires and saline) S4B6-1 antibody bound IL-2 selectively activates T cells expressing CD122 and not cells expressing CD25 as evidenced by proliferation marker Ki67 as well as a percentage of parent cell population. The % CD122 CD8+ cells increased substantially in the skin, as well as the proliferation of Natural Killer cells, both populations which express the relevant receptor. The CD25+ cell populations such as Tregs and Teffectors are unchanged, both in % of parent as well as in Ki67 mean fluorescence intensity, indicating that the antibody-IL-2 complex is selective for cognate receptor, whereas the equivalent concentration of antibody dosed subcutaneously has no effect in the skin over control. Little downstream activation of CD8's in the skin draining lymph nodes was observed, while the soluble antibody appears to wash away free IL-2 and decrease this cell type's activation—showing nanowires provide a selectively on target effect. (FIG. 11)

In Vivo Test if Mice with IL2 Nanowires

Immune response of injected S4B6-1 anti-IL2 nanowires were tested in vivo.

Materials
20 C57BL/6 mice
Digestion cocktail
For 15 mL:
  30 mg (2 mg/ml) collagenase XI (4129.2 U/ml, Sigma, # C9407-100 mg, Collagenase digestion activity 1240 U/mg),
  7.5 mg (0.5 mg/ml) hyaluronidase (260 U/ml, Sigma, # H3506-100 mg, 451 U/mg)
  1.5 mg (0.1 mg/ml, ICN) DNase (0.1 mg/ml, ICN)
Interventions:
  Nanoparticles only
  Nanoparticles+anti-IL2
  S4B6-1 Anti-IL2 only (50 ng)
  A488-IgG conjugated nanowires
Experimental Design

| Group | Mice | Treatment | Harvest |
|---|---|---|---|
| A | 6 female B6 | SQ Nanowires | Day 3 |
| B | 6 female B6 | SQ Nanowires + anti-IL2 | Day 3 |
| C | 6 female B6 | 50 ng anti-IL2 SQ | Day 3 |
| D (for imaging only) | 2 female B6 | SQ A488-IgG conjugated NWs | 1 mouse day 3, 1 mouse day 7 |

Protocol:
Day 0:
Anesthetize mice with isofluorane. Shave mice dorsal skin. Inject 50 µL of nanowires SQ in 10 injection sites on back.

Day 3:
Harvest mice
Mouse Harvest Protocol:
Sacrificed mouse. First remove skin draining lymph nodes (inguinal, axillary, and brachial), then remove skin from mouse. Harvest back skin only, aiming for area dosed with nanowires.
Digestion:
Scrape fat off of skin in petri dish using forceps. Weigh skin.
Skin: place in shallow top of petri dish. Put 0.5 mL aliquot of skin digestion cocktail onto skin to wet it. Mince skin with scissors until there is no resistance. Transfer to 50 mL conical with 3 mL digestion cocktail. When skin samples from all mice have been collected, put in 37 degree bacterial incubator to shake (250 RPM) for 45 minutes.
Lymph nodes: Mash with rubber end of syringe through 100 um filter, and wash filter/syringe with 8 mL C10 medium. Leave on ice until skin is processing. Spin down, resuspend at 10 mL C10 medium and count. Resuspend at 8×10^6 cells/mL.
Once finished processing, put on ice. Add 10 mL C10 and vortex and filter sample through 100 micron filter. Spin down (4 C, 5 min 1500 RPM). Remove supernatant and resuspend in 1 mL C10. Count on nucleocounter. Spin down and resuspend in at 16×10^6 cells/mL. Stain 1-2×10^6 cells with myeloid/i cell panel immediately.
1 million cells for each collective lymph node sample and 2 million cells for each skin sample are stained for flow cytometry. See flow panel for antibody type and stains.
Flow staining:
  1. Prepare surface antibody mix (50 μL excess) in PBS+ 2% FBS. Wash cells in plate in PBS+2% FBS. Spin down at 2000 RPM 4 C for 2 min.
  2. Remove supernatant and resuspend in 100 μL of Ab mix for skin and 50 μL Ab for LN.
  3. Incubate at 4 C for 30 minutes.
  4. Add 150 μL PBS/FBS and spin down as before. Wash 1× with 200 μL PBS/FBS.
  5. Reconstitute Fixation/Permeation solution (1:4) and add 50 μL of Fix/Perm (ebio).
  6. Incubate at 4 C for 30 minutes.
  7. Add 150 μL Perm wash, spin for 4 min at 4 degC 2000 RPM
  8. Prepare Ab mixes in Perm Buffer according to panel (50l in excess).
  9. Add 100 μl Ab mix to each skin sample and 50 μL for LN.
  10. Incubate 30 min at 4° C. in the dark
  11. Add 150 μl Perm Buffer to each sample
  12. Centrifuge for 4 min at 4° C. and 2000 rpm.
  13. Wash 1× with 200 μL Perm buffer, centrifuge as before.
  14. Resuspend in 150 μL PBS/FBS.
  15. Analyze on Flow Cytometry.
Cryosectioning: Locate nanowire nodule in dorsal skin skin section, trim to approx. 0.5 cm×0.5 cm and place in OCT inside cassette. Freeze in isopentane chilled by liquid nitrogen, then store at −80 C. Sectioning on cryostat at 20 um sections, stored at −20 C until section staining carried out.
Tissue Staining:
Buffers:
  1. Formaldehyde: 16%, methanol free, Polysciences, Inc. (cat#18814), use fresh and store opened vials at 4° C. in dark. Dilute 1 in 4 in 1×PBS to make a 4% formaldehyde solution.
  2. Blocking Buffer: (1×PBS/5% normal serum/0.3% Triton™ X-100): To prepare 10 ml, add 0.5 ml normal serum from the same species as the secondary antibody (e.g., Normal Goat Serum (#5425) to 9.5 ml 1×PBS) and mix well. While stirring, add 30 μl Triton™ X-100.
  3. Antibody Dilution Buffer: (1×PBS/1% BSA/0.3% Triton™ X-100): To prepare 10 ml, add 30 μl Triton™ X-100 to 10 ml 1×PBS. Mix well then add 0.1 g BSA (#9998), mix.
Block specimen in blocking buffer for 60 min.
  1. While blocking, prepare primary antibody by diluting as indicated on datasheet in antibody dilution buffer.
  2. Aspirate blocking solution, apply diluted primary antibody.
  3. Incubate overnight at 4° C.
  4. Rinse three times in 1×PBS for 5 min each.
     NOTE: If using a fluorochrome-conjugated primary antibody, then skip to Step 7.
  5. Incubate specimen in fluorochrome-conjugated secondary antibody diluted in antibody dilution buffer for 1-2 hr at room temperature in the dark.
  6. Rinse three times in 1×PBS for 5 min each.
  7. Coverslip slides with Prolong® Gold Antifade Reagent (#9071) or Prolong® Gold Antifade Reagent with DAPI (#8961).
  8. For best results, allow mountant to cure overnight at room temperature. For long-term storage, store slides flat at 4° C. protected from light.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:
1. A method for preparing a composition comprising individual polymeric nanowires, the method comprising:
    applying a polymer composition comprising a polymer to a surface of a substrate to produce a polymer-coated substrate;
    positioning a template structure comprising a plurality of pores onto the polymer-coated substrate;
    heating the polymer-coated substrate in a manner sufficient to melt the polymer and draw the polymer into the pores of the template structure until the template structure comes into direct contact with the substrate;

removing the template structure from the substrate, wherein the template structure comprises formed polymeric nanowires; and etching the removed template structure to dissolve the template structure and produce a composition comprising individual polymeric nanowires, wherein the individual polymeric nanowires are discrete nanowires and are not connected together.

2. The method according to claim 1, wherein etching the template structure comprises dissolving the template structure with a base.

3. The method according to claim 2, wherein the template structure is broken up into a plurality of pieces and the plurality of pieces are dissolved in the base.

4. The method according to claim 2, wherein the base is sodium hydroxide.

5. The method according to claim 1, further comprising flattening the polymer-coated substrate prior to positioning the template structure on the polymer-coated substrate.

6. The method according to claim 5, wherein flattening comprises removing solvent from the polymer composition.

7. The method according to claim 5, wherein flattening comprises heating the polymer-coated substrate.

8. The method according to claim 1, wherein the polymer-coated substrate is heated to a temperature that is from 5° C. to 100° C. above the melting temperature of the polymer.

9. The method according to claim 1, wherein pressure is applied to the template structure to draw the polymer into the pores of the template structure.

10. The method according to claim 1, wherein the template structure comprises a porous membrane.

11. The method according to claim 10, wherein the porous membrane is a porous metal membrane.

12. The method according to claim 11, wherein the porous membrane is a porous metal oxide membrane.

13. The method according to claim 12, wherein the porous membrane is a porous aluminum oxide membrane.

14. The method according to claim 1, further comprising purifying the composition comprising individual polymeric nanowires.

15. The method according to claim 14, wherein purifying comprises sonicating the composition and filtering the composition comprising individual polymeric nanowires with deionized water or a buffer solution.

16. The method according to claim 1, wherein the polymer comprises a polyester.

17. The method according to claim 16, wherein the polymer comprises polycaprolactone.

18. The method according to claim 1, wherein the polymer has a molecular weight of from 5 kDa to 250 kDa.

19. The method according to claim 18, wherein the polymer is polycaprolactone having a molecular weight of from 40 kDa to 80 kDa.

20. The method according to claim 1, wherein the individual polymeric nanowires have a diameter of from 10 nm to 500 nm.

21. The method according to claim 20, wherein the individual polymeric nanowires have a diameter of about 200 nm.

22. The method according to claim 1, wherein the individual polymeric nanowires have a length of from 1 µm to 50 µm.

23. The method according to claim 22, wherein the individual polymeric nanowires have a length of from 10 µm to 20 µm.

24. The method according to claim 1, wherein the aspect ratio of the individual polymeric nanowires is 2 or higher.

25. The method according to claim 24, wherein the aspect ratio of the individual polymeric nanowires is 5 or higher.

26. The method according to claim 1, wherein the individual polymeric nanowires do not have a lumen.

27. The method of claim 2, wherein the template structure with the formed polymeric nanowires is shaken, vortexed or sonicated while in the base to release the polymeric nanowires into solution.

28. The method of claim 1, wherein removing the template structure comprises using a blade to remove the template structure from the substrate.

29. The method of claim 28, further comprising allowing the polymer to cool overnight prior to removing the template structure from the substrate.

* * * * *

UNITED STATES PATENT AND TRADEMARK OFFICE
CERTIFICATE OF CORRECTION

PATENT NO. : 11,278,626 B2
APPLICATION NO. : 16/338103
DATED : March 22, 2022
INVENTOR(S) : Colin R. Zamecnik et al.

It is certified that error appears in the above-identified patent and that said Letters Patent is hereby corrected as shown below:

In the Specification

In Column 7, Line 19, "of greater" should read --or greater--.

In Column 25, Line 19, "bicalutarnide" should read --Bicalutamide--.

Signed and Sealed this
Twenty-fourth Day of May, 2022

Katherine Kelly Vidal
Director of the United States Patent and Trademark Office